United States Patent
Gelfand et al.

(10) Patent No.: US 10,299,714 B2
(45) Date of Patent: May 28, 2019

(54) BLOOD COLLECTION DEVICES CONTAINING BLOOD STABILIZATION AGENT INCLUDING VARIEGIN OR ANALOG THEREOF AND/OR A POLYSULFATED DISACCHARIDE

(75) Inventors: Craig A. Gelfand, Jackson, NJ (US); Daniel Marchiarullo, Morris Plains, NJ (US); Keith Moskowitz, Monroe, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1850 days.

(21) Appl. No.: 13/310,084

(22) Filed: Dec. 2, 2011

(65) Prior Publication Data

US 2012/0149004 A1    Jun. 14, 2012

Related U.S. Application Data

(60) Provisional application No. 61/419,063, filed on Dec. 2, 2010.

(51) Int. Cl.
*A61B 5/15* (2006.01)
*B01L 3/00* (2006.01)
*A61B 5/154* (2006.01)

(52) U.S. Cl.
CPC .......... *A61B 5/154* (2013.01); *A61B 5/15003* (2013.01); *A61B 5/150251* (2013.01); *A61B 5/150305* (2013.01); *A61B 5/150351* (2013.01); *A61B 5/150755* (2013.01); *B01L 3/5082* (2013.01)

(58) Field of Classification Search
None
See application file for complete search history.

(56) References Cited

U.S. PATENT DOCUMENTS

| | | |
|---|---|---|
| 5,498,601 A | 3/1996 | Sato et al. |
| 6,143,719 A | 11/2000 | Schmaier et al. |
| 6,544,750 B1 | 4/2003 | Schmaier et al. |
| 6,982,249 B1 | 1/2006 | Schmaier et al. |
| 7,074,765 B2 | 7/2006 | Schmaier et al. |
| 7,309,468 B2 | 12/2007 | Stevens et al. |
| 7,879,792 B2 | 2/2011 | Schmaier et al. |
| 9,217,027 B2 * | 12/2015 | Kazimtrova ........... A61K 38/36 |

(Continued)

FOREIGN PATENT DOCUMENTS

| | | |
|---|---|---|
| CN | 1053192 A | 7/1991 |
| CN | 1568307 A | 1/2005 |

(Continued)

OTHER PUBLICATIONS

US 5,006,107 A, 04/1991, Robinson et al. (withdrawn)

(Continued)

*Primary Examiner* — Richard A Schnizer
*Assistant Examiner* — Gary E Hollinden
(74) *Attorney, Agent, or Firm* — Botos Churchill IP Law LLP

(57) ABSTRACT

Disclosed are devices for collecting and stabilizing blood that contain a blood stabilization agent which includes variegin or an analog thereof, a polysulfated disaccharide, or a combination thereof, each in an amount effective to stabilize blood. Methods of making and using the devices, and kits containing the devices, are also provided.

16 Claims, 4 Drawing Sheets

Specification includes a Sequence Listing.

(56) References Cited

U.S. PATENT DOCUMENTS

| | | | |
|---|---|---|---|
| 2004/0013575 A1 | | 1/2004 | Stevens et al. |
| 2004/0019021 A1 | * | 1/2004 | Banwell ............... C07C 215/44 514/114 |
| 2004/0137417 A1 | | 7/2004 | Ryan |
| 2007/0219131 A1 | * | 9/2007 | Ben-Sasson ......... A61K 9/0014 424/450 |
| 2009/0123907 A1 | | 5/2009 | Shanbrom |
| 2010/0278752 A1 | * | 11/2010 | Kotsyfakis et al. ......... 424/9.81 |
| 2011/0014701 A1 | * | 1/2011 | Ghosh .................. C12N 5/0663 435/374 |
| 2012/0135931 A1 | * | 5/2012 | Kini et al. ................... 514/13.7 |
| 2013/0183237 A1 | * | 7/2013 | Kazimirova et al. ........ 424/1.69 |

FOREIGN PATENT DOCUMENTS

| | | |
|---|---|---|
| CN | 1662307 A | 8/2005 |
| CN | 1703621 A | 11/2005 |
| CN | 1846603 A | 10/2006 |
| EP | 2185185 A2 | 5/2010 |
| GB | 00711779 A | 7/1954 |
| JP | 60053845 | 3/1985 |
| JP | H06192291 A | 7/1994 |
| JP | H08104617 A | 4/1996 |
| JP | 2005525126 A | 8/2005 |
| JP | 2008185564 A | 8/2008 |
| JP | 2010530238 A | 9/2010 |
| WO | 9303748 A1 | 3/1993 |
| WO | 94005696 A1 | 3/1994 |
| WO | 9641640 A1 | 12/1996 |
| WO | 9847522 A1 | 10/1998 |
| WO | 0112656 A1 | 2/2001 |
| WO | 0228825 A2 | 4/2002 |
| WO | 03095974 A2 | 11/2003 |
| WO | 2003097237 A2 | 11/2003 |
| WO | 2004098628 A2 | 11/2004 |
| WO | 2006130718 A2 | 12/2006 |
| WO | 2008155658 A2 | 12/2008 |

OTHER PUBLICATIONS

Wall et al., "Characterisation of the anticoagulant properties of a range of structurally diverse sulfated oligosaccharides", Thrombosis Research (2001) 103:325-335.*

International Search Report and Written Opinion for Application No. PCT/US2011/063086 dated Jul. 31, 2012.

Qiao et al., "Archieving structural diversity using the perpendicular conformation of alpha-substituted phenylcyclopropanes to mimic the bioactive conformation of ortho-substituted biphenyl P4 moieties: Discovery of novel, highly potent inhibitors of Factor Xa", Bioorganic & Medicinal Chemistry Letters 18 (2008) 4118-4123.

Koh et al., "Variegin, a Novel Fast and Tight Binding thrombin Inhibitor from the Tropical Bont Tick", The Journal of Bilological Chemistry vol. 282, No. 40, pp. 29101-29113, Oct. 5, 2007.

Chinese Office Action for Application No. 201180058163.X dated Sep. 29, 2014.

Hellstern, "Preservation of in vitro function of platelets stored in the presence of a synthetic dual inhibitor of factor Xa and thrombin", Journal of Thrombosis and Haemostasis, 5: 2119-2126.

Examination Report received in corresponding in application No. 4740/DELNP/2013, dated Sep. 28, 2018, pp. 5.

* cited by examiner

SEQUENCE LISTING

<160> NUMBER OF SEQ ID NOS: 17

<210> SEQ ID NO 1
<211> LENGTH: 32
<212> TYPE: PRT
<213> ORGANISM: Artificial Sequence
<220> FEATURE:
<223> OTHER INFORMATION: Synthetic Peptide: Variegin Fragment

<400> SEQUENCE: 1

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu Asp Asp Glu Ser

<210> SEQ ID NO 2
<211> LENGTH: 29
<212> TYPE: PRT
<213> ORGANISM: Artificial Sequence
<220> FEATURE:
<223> OTHER INFORMATION: Synthetic Peptide: Variegin Fragment

<400> SEQUENCE: 2

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu Asp
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic Peptide: Variegin Fragment

<400> SEQUENCE: 3

Ser Asp Gln Gly Asp Val Ala Glu Pro Lys Met His Lys Thr Ala Pro
1               5                   10                  15

Pro Phe Asp Phe Glu Ala Ile Pro Glu Glu
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide: Variegin Fragment

<400> SEQUENCE: 4

Gly Asp Val Ala Glu Pro Lys Met His Lys Thr Ala Pro Pro Phe Asp
1               5                   10                  15

Phe Glu Ala Ile Pro Glu Glu Tyr Leu Asp Asp Glu Ser
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide: Variegin Fragment

<400> SEQUENCE: 5

Asp Gln Gly Asp Val Ala Glu Pro Lys Met His Lys Thr Ala Pro Pro
1               5                   10                  15

Phe Asp Phe Glu Ala Ile Pro Glu Glu Tyr Leu
            20                  25

<210> SEQ ID NO 6
<211> LENGTH: 32
<212> TYPE: PRT
<213> ORGANISM: Artificial Sequence
<220> FEATURE:
<223> OTHER INFORMATION: Synthetic Peptide: Variegin Fragment

<400> SEQUENCE: 6

Ser Asp Gln Gly Asp Val Ala Glu Pro Ala Met His Lys Thr Ala Pro
1               5                   10                  15

```
Pro Phe Asp Phe Glu Ala Ile Pro Glu Glu Tyr Leu Asp Asp Glu Ser
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: Synthetic Peptide: Variegin Fragment

<400> SEQUENCE: 7

Ser Asp Gln Ala Asp Arg Ala Gln Pro Lys Leu His Arg Asn Ala Pro
1               5                   10                  15

Gln Gly Asp Phe Glu Ala Ile Pro Asp Glu Tyr Leu
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic Peptide: Variegin Fragment

<400> SEQUENCE: 8

Ser Asp Gln Ser Gly Arg Ala Gln Pro Lys Leu Pro Arg Asn Ala Pro
1               5                   10                  15

Gln Gly Asp Phe Glu Ala Ile Pro Asp Glu Tyr Leu
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic Peptide: Variegin Fragment

<400> SEQUENCE: 9

Ser Asp Gln Gly Asp Val Ala Glu Pro Lys Met His Lys Thr Ala Pro
1               5                   10                  15

Pro Gly Asp Phe Glu Ala Ile Pro Glu Glu Tyr Leu Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Peptide: Variegin Fragment

<400> SEQUENCE: 10

Ser Asp Gln Ala Asp Val Ala Glu Pro Lys Met His Lys Thr Ala Pro
1               5                   10                  15

Pro Gly Asp Phe Glu Ala Ile Pro Glu Glu Tyr Leu Asp
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Peptide: Variegin Fragment

<400> SEQUENCE: 11

Glu Pro Lys Met His Lys Thr Ala Pro Pro Phe Asp Phe Glu Ala Ile
1               5                   10                  15
```

Pro Glu Glu Tyr Leu Asp Asp Glu Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Peptide: Variegin Fragment

<400> SEQUENCE: 12

Glu Pro Lys Met His Lys Thr Ala Pro Pro Phe Asp Phe Glu Glu Ile
1               5                   10                  15

Pro Glu Glu Tyr Leu Asp Asp Glu Ser
            20                  25

<210> SEQ ID NO 13
<211> LENGTH: 21
<212> TYPE: PRT
<213> ORGANISM: Artificial Sequence
<220> FEATURE:
<223> OTHER INFORMATION: Synthetic Peptide: Variegin Fragment

<400> SEQUENCE: 13

Glu Pro Lys Met His Lys Thr Ala Pro Pro Phe Asp Phe Glu Ala Ile
1               5                   10                  15

Pro Glu Glu Tyr Leu
            20

<210> SEQ ID NO 14
<211> LENGTH: 18
<212> TYPE: PRT
<213> ORGANISM: Artificial Sequence
<220> FEATURE:
<223> OTHER INFORMATION: Synthetic Peptide: Variegin Fragment

<400> SEQUENCE: 14

Met His Lys Thr Ala Pro Pro Phe Asp Phe Glu Ala Ile Pro Glu Glu
1               5                   10                  15

Tyr Leu

<210> SEQ ID NO 15
<211> LENGTH: 24
<212> TYPE: PRT
<213> ORGANISM: Artificial Sequence
<220> FEATURE:
<223> OTHER INFORMATION: Synthetic Peptide: Variegin Fragment

<400> SEQUENCE: 15

Asp Val Ala Glu Pro Lys Met His Lys Thr Ala Pro Pro Phe Asp Phe
1               5                   10                  15

Glu Ala Ile Pro Glu Glu Tyr Leu
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic Peptide: Variegin Fragment

<400> SEQUENCE: 16

Asp Val Ala Glu Pro Arg Met His Lys Thr Ala Pro Pro Phe Asp Phe
1               5                   10                  15

```
Glu Ala Ile Pro Glu Glu Tyr Leu
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic Peptide: Variegin Fragment

<400> SEQUENCE: 17

Met His Lys Thr Ala Pro Pro Phe Asp Phe Glu Ala Ile Pro Glu Glu
1               5                   10                  15

Tyr Leu Asp Asp Glu Ser
            20
```

BLOOD COLLECTION DEVICES CONTAINING BLOOD STABILIZATION AGENT INCLUDING VARIEGIN OR ANALOG THEREOF AND/OR A POLYSULFATED DISACCHARIDE

CROSS-REFERENCE TO RELATED APPLICATION

The present application claims the benefit of the filing date of U.S. Provisional Patent Application No. 61/419,063 filed Dec. 2, 2010, the disclosure of which is hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 30, 2011, is named Sequence Listing for Blood Collection Devices_ST25.txt and is 6.18 kilobytes in size.

BACKGROUND OF THE INVENTION

Human blood is evaluated in vitro for a broad array of diagnostic purposes. Blood is composed of blood cells and plasma. Platelets, which are the smallest of the three major types of blood cells, are only about 20% of the diameter of red blood cells, the most numerous cell of the blood. The normal platelet count is 150,000-350,000 per microliter of blood but since platelets are so small, they make up just a tiny fraction of the blood volume. A principal function of platelets is to maintain homeostasis of blood and prevent bleeding. Platelet function is therefore one indicator of blood homeostasis.

Blood homeostasis refers to the preservation of the bloodstream in an intact and normally functioning manner. This includes maintenance of the chemical properties of blood, and the intactness of blood and vasculature. In the event of an interruption of vascular intactness, for example from a cut, trauma, surgery, or other events that typically cause "bleeding", a cascade of cellular and biochemical processes within the blood is initiated, with the ultimate goal of preventing or minimizing loss of blood. A visual endpoint of this biological response is the formation of a scab. At a molecular and cellular level, the processes involve interactions between proteins normally circulating in blood and platelets. Several proteins in blood, as well as the platelets themselves, react to exposure to a protein called "tissue factor" which is present in many other tissues throughout the body, but notably is absent from the inside of the veins and arteries comprising normal vasculature. Through direct and indirect chemical pathways, platelets respond to the presence of tissue factor by aggregating, an irreversible (or "one time only") process by which they dramatically change shape and actively bind each other. This process is known as platelet aggregation. Other enzymes in the blood also react and start to alter proteins in the blood, which start to form insoluble fibrous masses. Analogous to filling a hole with spackle, these insoluble mixtures of proteins, platelets, and other blood components occlude the "hole" in the vascular wall, and, in simple terms, "stop the bleeding".

More scientifically, when exposed to a damaged blood vessel, platelets will adhere to exposed sub-endothelial matrix. Following the initial adhesion, various factors are released or produced at the site of injury (including thrombin, ADP, growth factors, and collagen) which activate the platelets. Once platelets are activated, a conformational change occurs in the platelet glycoprotein GPIIb/IIIa receptor, allowing it to bind fibrinogen and/or von Willebrand factor. It is believed that this binding of the multivalent fibrinogen and/or von Willebrand factor molecules by GPIIb/IIIa receptors on adjacent platelets results in the recruitment of additional platelets to the site of injury and their aggregation to form a hemostatic plug or thrombus. Platelet aggregation is a term used to describe the binding of platelets to one another. Platelet aggregation is also associated with degranulation, a process through which granules ("envelopes" that contain proteins and small molecules) are released into the surrounding plasma. This process is known as degranulation. These granule contents serve to further accelerate restoration of hemostasis and stimulate cell repair (healing) processes on the vascular wall and any non-vascular tissue.

Without a sufficient number of platelets, or in cases where normal platelet function is impaired or even absent, there is a significant risk of extensive bleeding. Platelet transfusions are administered to patients who have undergone severe trauma, or in cases of emergency surgery where there has been extensive loss of blood.

Understandably, measurements of the ability of platelets to aggregate and thus facilitate or accelerate blood clotting can be important in a number of clinical settings.

It is known that platelet aggregation plays a key role in the pathogenesis of thrombosis and acute coronary artery disease. Evidence suggests that significant variation in inhibition of platelet function exists in the response to various antiplatelet agents. It has also been demonstrated that an inter-individual variability in platelet aggregation exists when P2Y12 antagonists, such as clopidogrel (Plavix), are used for treatment of patients to achieve an anti-aggregation effect. For example, the results of one study demonstrated that at least 10% of patients receiving the drug did not achieve the expected platelet aggregation inhibition (Muller et al., Thromb Haemost. 89(5):783-7 (2003)). Thus, given the acute nature of adverse cardiovascular events, it can be critical to know that the first therapeutic approach selected for a patient will have immediate benefit, ideally without having to monitor the patients and be forced to select alternative therapies. Thus, before patients undergo such therapy, they often have blood samples drawn and tested for platelet function. Similar testing is often employed for pre-surgical screening to rule out potential adverse bleeding effects during surgery/recovery.

It is also desirable to stabilize platelets in drawn blood samples for purposes of testing for disease biomarker testing. Platelets contain proteins and metabolites of diagnostic interest. However, the concentration of the freely circulating forms of these biomarkers in plasma is much more relevant for purposes of diagnosing disease conditions. It is believed that degranulation of platelets, especially upon platelet activation or aggregation, can lead to artificially elevated levels of these markers and represents a preanalytical error if not controlled. The platelet granules also contain enzymes which can catalyze degradation of these circulating biomarkers, and thus result in artificially low levels of the biomarkers of interest.

Further, it is desirable to provide stable platelets for use in therapeutic applications. Autologous platelet gel therapy (which involves isolation of so-called "platelet-rich plasma") is used to treat certain wounds and a wide range of other conditions ranging from dental implant healing to injections intended to repair ligament damage. If platelets aggregate or become prematurely activated, they may lose this therapeutic effect. As such, there is a need to provide stabilized platelets which could further enhance these processes.

Results of in vitro platelet function can be inaccurate if the platelets are not stabilized in the drawn blood sample, either allowing them to aggregate prior to testing (e.g., no function "left" to test for), or perhaps to "die" or otherwise lose natural function prior to testing. Platelets are inherently unstable in drawn blood, principally because their natural role is to aggregate in response to disruption of the vasculature. Chemical stimulation of platelet aggregation will happen spontaneously at a low level in a drawn blood sample. Over time after the blood is drawn, the platelets aggregate because of this spontaneous stimulation, and so there are fewer and fewer platelets in their original state that are still able to be stimulated whenever the blood sample is finally going to be tested. The current gold-standard of clinical practice calls for platelet function testing to be done on a citrate-anticoagulated blood sample within a maximum of 2 to 4 hours after blood draw (Clinical Laboratory Standards Institute Guideline, "Platelet Function Testing by Aggregometry, H58-A (Vol. 28, No. 31 (2008)). After this time, the sample will have lost much of its original platelet function that it might not be usable for clinical measurements. This widely applied operational standard limits the broad-market utility of platelet function testing. In current practice, for example, many blood samples are sent out from physician's offices to regional testing facilities and may not be tested for many hours or possibly even days after being drawn.

Thus, a need remains for stabilizing blood and blood components such as platelets in compositions such as collected blood samples that better preserves function after collection and during storage or transport, prior to analysis.

BRIEF SUMMARY OF THE INVENTION

One aspect of the present invention is directed to a device for collecting and stabilizing blood (e.g., a whole blood sample) or a composition containing a component of blood (e.g., a cellular component such as white blood cells or platelets) that has a first end and a second end and at least one interior wall defining a reservoir portion for receiving the blood or component thereof. The reservoir contains a blood stabilization agent which includes variegin or an analog thereof, a polysulfated disaccharide (such as sucrose octasulfate), or a combination thereof, each in an amount effective to stabilize blood, e.g., preserving platelet function such as their ability to aggregate. Although embodiments of the present invention describe platelet function as a measure of blood stability, the skilled person will appreciate that there are other manifestations of the relative stability or instability of a blood sample as measured by other blood parameters (e.g., levels of analytes in the plasma or serum, cell count, cellular stability, cellular intactness, hemolysis, etc). In some embodiments, the device is fitted with a closure pierceable by a needle (e.g., for supplying blood to the reservoir) and is sterile and evacuated.

Another aspect of the present invention is directed to a method for collecting and stabilizing blood or a composition containing a component thereof (e.g., a cellular component such as white blood cells or platelets), comprising introducing the blood or the composition into a device that has a first end and a second end and at least one interior wall defining a reservoir portion for receiving the blood or composition, and a blood stabilization disposed in the reservoir, wherein the blood stabilization agent includes variegin or an analog thereof, a polysulfated disaccharide (e.g., sucrose octasulfate), or a combination thereof, each in an amount effective to stabilize blood, e.g., preserving platelet function such as their ability to aggregate. Subsequent to collection and storage, the blood or the composition may be utilized, e.g., for diagnostic analysis or therapeutic purposes.

A further aspect of the present invention is directed to a method for measuring a parameter of blood function (e.g., platelet function) in vitro, comprising: a) introducing a blood or a composition comprising a component of blood (e.g., platelets) into device for collecting and stabilizing platelets, wherein the device has a first end and a second end and at least one interior wall defining a reservoir portion for receiving the blood or composition, wherein the reservoir contains a blood stabilization agent comprising variegin having the amino acid sequence designated as SEQ ID NO:1, or an analog thereof, a polysulfated disaccharide, or a combination thereof, each in an amount effective to stabilize blood, e.g., preserving platelet function such as their ability to aggregate, and b) measuring the blood parameter. In some embodiments in which the blood parameter pertains to platelet function, the method may further entail c) adding to the composition a platelet agonist that stimulates aggregation of the platelets, and c) measuring extent of platelet aggregation, wherein extent of platelet aggregation induced by the agonist is determinative of platelet function.

A further aspect of the present invention is directed to a package or kit that includes at least one such device (and preferably a plurality of such devices).

While variegin and polysulfated disaccharides such as sucrose octasulfate have been reported for therapeutic use based on their ability to inactivate thrombin in vivo (and in vitro), the present applicants have discovered (as shown in the working examples) that thrombin inhibitory activity is not in and of itself predictive of the ability of a given agent to stabilize blood or its components, and particularly platelets, contained in a collected blood sample, for any extended, clinically meaningful time. Without intending to be bound by any particular theory of operation, Applicants hypothesize that the activity of a given thrombin inhibitor in vivo is not predictive of how it will perform in a non-physiological environment such as a collected blood sample or a composition containing a blood component such as platelets (e.g., a platelet-rich plasma (PRP)), and particularly from the standpoint of its ability to preserve platelet function, and thus preserve the intactness of the sample for purposes of storage and subsequent analysis.

DETAILED DESCRIPTION

Broadly, the collection devices of the present invention can encompass any collection device including tubes such as test tubes and centrifuge tubes; closed system blood collection devices, such as collection bags; syringes, especially pre-filled syringes; catheters; microtiter and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips; tissue and other biological sample collection containers; and any other container suitable for holding a biological sample, as well as containers and elements involved in transferring samples. Examples and illustrations of several such devices are disclosed in commonly owned U.S. Pat. No. 7,309,468 to Stevens et al. The device may be evacuated and sterile, and include a closure pierceable by a needle. Alternatively, the device may be a partially-evacuated or a non-evacuated system for collecting blood. A suitable example of an evacuated system is a closed tube. A manual syringe draw is a suitable example of both a partially-evacuated and a non-evacuated system. Non-evacuated systems may also include automatic draw systems.

Figure 1:
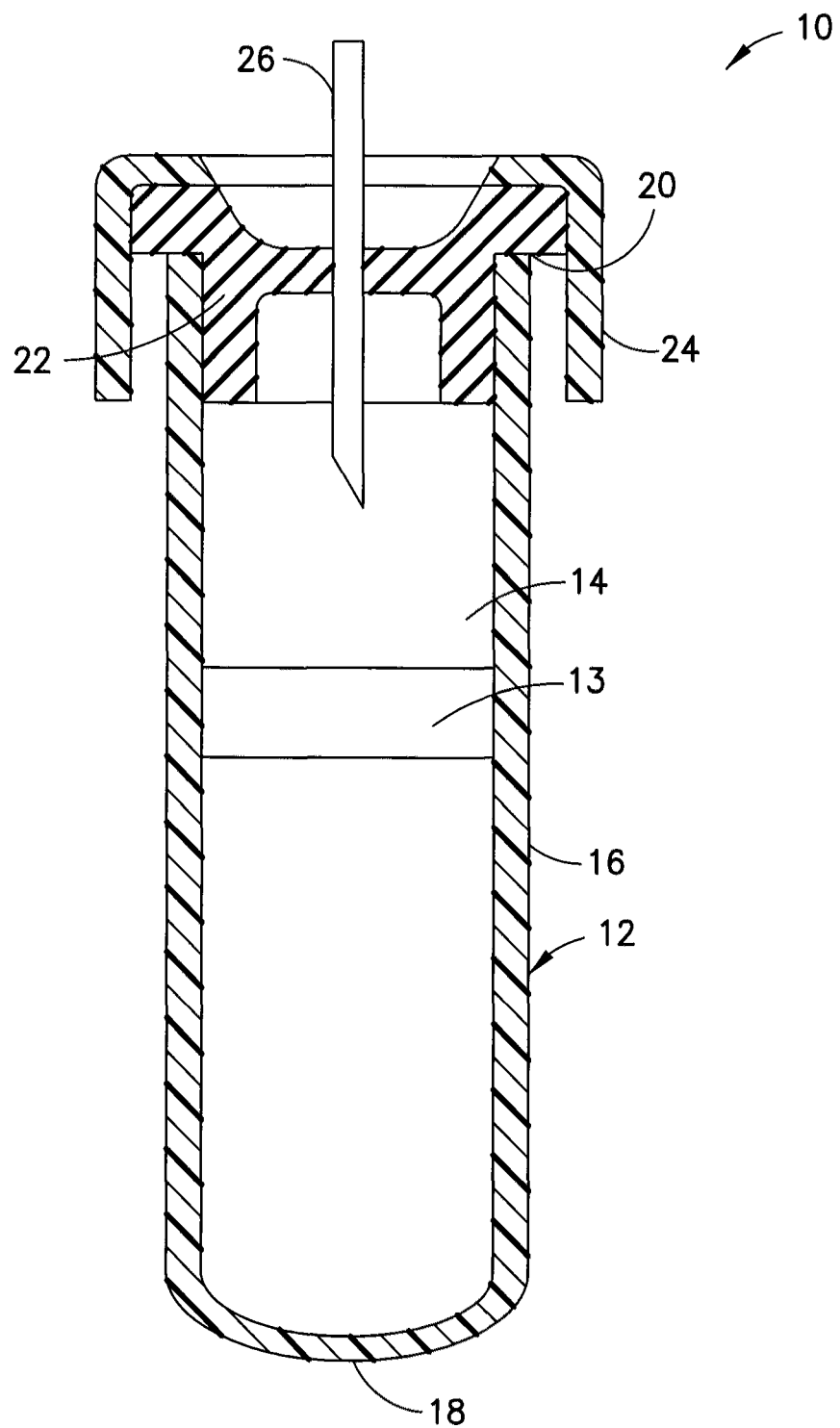
FIG. 1 is a perspective view of a device suitable for use in the present invention.

FIG. 1, which is also illustrated in U.S. Pat. No. 7,309,468, shows a typical blood collection device 10, useful in the present invention, which includes a container 12 defining an internal chamber or reservoir 14. In the embodiment illustrated, container 12 is a hollow tube having a side wall 16, a closed bottom end 18 and an open top end 20. Optionally, a separating member 13 is provided within the container chamber 14. Separating member 13 serves to assist in separating components of the blood sample, for example, by centrifugation. Container 12 is dimensioned for collecting a suitable volume of blood. A closure means 22 for covering open end 20 to close container 12 is necessary where a sterile product is demanded. In some embodiments, the tube is configured for a screw cap. Preferably, closure 22 forms a seal capable of effectively closing container 12 and retaining a biological sample in chamber 14. Closure 22 may be one of a variety of forms including, but not limited to, rubber closures, HEMOGUARD™ closures, metallic seals, metal-banded rubber seals and seals of different polymers and designs. A protective shield 24 may overlie closure 22.

Container 12 can be made of any material suitable for laboratory vessels, including, for example plastics (e.g., polyolefins, polyamides, polyesters, silicones, polyurethanes, epoxies, acrylics, polyacrylates, polyesters, polysulfones, polymethacrylates, PEEK, polyimide and fluoropolymers) and glass products including silica glass. Preferably, container 12 is transparent. Examples of suitable transparent thermoplastic materials for container 12 include polycarbonates, polyethylene, polypropylene and polyethyleneterephthalate. Plastic materials can be oxygen-impermeable materials or may contain an oxygen-impermeable or semi-permeable layer. Alternatively, container 12 can be made of a water and air permeable plastic material.

The pressure in chamber 14 is selected to draw a predetermined volume of biological sample into chamber 14. Preferably, closure 22 is made of a resilient material that is capable of maintaining the internal pressure differential between atmospheric pressure and a pressure less than atmospheric. Closure 22 is such that it can be pierced by a needle 26 or other cannula to introduce a biological sample into container 12 as known in the art. Preferably, closure 22 is resealable. Suitable materials for closure 22 include, for example, silicone rubber, natural rubber, styrene butadiene rubber, ethylene-propylene copolymers and polychloroprene.

Suitable examples of container 12 include single-wall and multi-layer tubes. A more specific example of a suitable container 12 is disclosed in U.S. Pat. No. 5,860,937.

Container 12 may also contain a separator 13 such as a gel, a mechanical separator or other type of separating member (e.g., filter paper or the like). Separators are typically useful for blood plasma preparation, specifically to separate plasma from human or animal whole blood. In some embodiments, the separator has a density that is intermediate between white cells and platelets, and which may be useful in isolation of PRP from the other cellular elements of a whole blood sample. The gel is desirably a thixotropic polymeric gel formulation. The gel may be a homopolymer or a copolymer and may include silicone-based gels such as, for example, polysiloxanes, or organic hydrocarbon-based gels such as, for example, polyacrylics, polyesters, polyolefins, oxidized cis polybutadienes, polybutenes, blends of epoxidized soybean oil and chlorinated hydrocarbons, copolymers of diacids and propandiols, hydrogenated cyclopentadienes and copolymers of alpha-olefins with dialkylmaleates. Examples of mechanical separators that may be useful in the present invention are described in U.S. Pat. Nos. 6,516,953; 6,406,671; 6,409,528; and 6,497,325.

Container 12 may also be adapted for centrifugally separating lymphocytes and monocytes from heavier phases of a sample of whole blood. In such embodiments, the devices may also contain a liquid density gradient medium and a means for preventing mixing of the liquid density gradient medium with a blood sample prior to centrifugation. An example of a suitable lymphocyte/monocyte collection tube is disclosed in U.S. Pat. No. 5,053,134.

Aside from the embodiment illustrated in FIG. 1, other commercially available blood collection tubes suitable for use in the present invention include the following, all of which are sold by Becton, Dickinson and Company (Franklin Lakes, N.J.), with all registrations and trademarks belonging to Becton, Dickinson and Company: VACUTAINER® hematology tubes (e.g., catalog nos. 367650-1, 367661, 6405, 6385, 6564, 367653, 367665, 367658, 367669, 6450-8, 6535-37 and 367662); VACUTAINER® K$_2$EDTA tubes (e.g., catalog nos. 367841-2, 367856 and 367861); and non-evacuated BD Microtainer® Tubes with BD Microgard™ Closure (e.g., 365987, 365965, and 365974) or conventional BD Microtainer® Tubes (e.g., 365956, 365957, 365958, 365959, 365971, and 365973). Many commercial blood collection tubes have standard volumes typically ranging from 250 microliters through and including about 10.0 ml, and in some cases up to 16 ml. Typical volumes include 250, 400, and 500 microliters, as well as 2.0 ml, 3.5 ml, 4.0 ml, 5.0 ml, 8.0 ml, 8.5 ml, and 10.0 ml.

In other embodiments, the device may include a reservoir integrated within a testing cartridge, the reservoir capable of holding a volume of whole blood in the range of 2 through 200 microliters, more preferably 50-150 microliters. Such cartridges are sold for instance under the trade name i-STAT Point of Care System by Abbott Laboratories (Abbott Park, Ill.), and are usable with a hand-held analyzer capable of interfacing with the cartridge. Examples of such cartridges and handheld analyzers usable with the present invention include the i-STAT CHEM8+ cartridge and i-STAT® 1 handheld analyzer respectively. Such devices are taught for examples in U.S. Pat. Nos. 5,096,669, 5,112,455, 5,821,399, 5,628,961, 7,419,821, 6,750,053, and U.S. D337,164.

In some embodiments, the device is a syringe. A syringe assembly may include a barrel having an open proximal end, a distal end and a sterile hollow chamber between the proximal and distal ends for receiving blood; a plunger located in the open proximal end; a needle secured to the barrel; and a platelet stabilizing agent within the chamber.

The devices of the present invention may be made or assembled in accordance with materials, reagents and processes known in the art. By way of example, one such method involves adding a platelet stabilization at least one platelet stabilizing agent (which as described herein may be in dried or lyophilized form) in an amount effective to stabilize platelets into the device; and then optionally adding a separating member to the device, and evacuating and/or sterilizing the device.

A representative lyophilization/evacuation process may entail the steps of freezing the device at a temperature of about −40° C. at a pressure of about 760 mm for about 6 to 8 hours; drying the device as the temperature is increased from −40° C. to about 25° C., at a pressure of about 0.05 mm, for about 8 to 10 hours; and then evacuating the device at a temperature of about 25° C. and a pressure of about 120 mm for about 0.1 hours, and then sterilizing the device, e.g., with cobalt 60 radiation. Additives and anti-coagulants may be added to the tube in a liquid form, and subsequently dried in this manner.

As used herein, the terms "blood" and "blood sample" refer to whole blood, or a component thereof (e.g., a composition such as another body tissue or fluid that contains a component of blood), particularly a cellular component thereof, including for example, red blood cell concentrates, platelet concentrates (e.g., platelet-rich plasma (PRP)), leukocyte concentrates; or plasma and serum. Thus, in other embodiments, the sample may be a body fluid or tissue containing blood cells or immature blood cells, such as bone marrow.

In some embodiments, the blood stabilizing agent is a naturally occurring or synthetic peptide extracted or derived from the salivary glands of haematophagous arthropods, preferably from the salivary glands of a tick, and most preferably from the salivary glands of *Amblyomma variegatum*. Such peptides are disclosed in WO29017699, WO03091284, and WO28155658. Such peptides are also disclosed in Cho, et al., J. Biol. Chem. 282(40):29101-13 (2007). Variegin and its analogs are "direct thrombin inhibitors", which as known in the art, refers to agents that bind the active site of thrombin and can thus inactivate both soluble and fibrin-bound thrombin.

In some embodiments, the blood stabilizing agent has the 32-amino acid sequence $NH_2$—SDQGDVAEPKMHKTAPPFDFEAIPEEYLDDES-acid, designated as SEQ. ID NO:1 (and referred to herein as variegin). Functional equivalents or analogs of variegin, which for purposes of the present invention, include variants, fragments (and variants thereof) and derivatives of SEQ ID NO:1, may also be useful in the present invention, provided that they retain the requisite platelet stabilization activity. Fragments of variegin will typically be identical to SEQ ID NO:1 except for the loss of 1, 2, 3, 4, 5, 6, 7, 8, 9 or 10 amino acids from the N-terminus and 1, 2, 3, 4, 5, 6, 7, 8, 9, 10 or even more amino acids from the C-terminus of the variegin protein sequence.

Variants of variegin will typically contain conservative amino acid substitutions compared to SEQ ID NO:1. Typical such substitutions are among Ala, Val, Leu and Ile; among Ser and Thr; among the acidic residues Asp and Glu; among Asn and Gln; among the basic residues Lys and Arg; or among the aromatic residues Phe, Trp and Tyr. In some embodiments, the amino acid substitutions are at positions 4, 5, 6, 8, 10, 11, 12, 13, 14, 17, 18, 22, 25 and 31 of SEQ ID NO:1. Thus, in some embodiments, the variegin variant differs from SEQ ID NO:1 in terms of one or more of the following substitutions: Gly at position 4 is replaced by Ala or Ser; Asp at position 5 is replaced by Gly; Val at position 6 is replaced by Arg; Glu at position 8 is replaced by Gln; Lys at position 10 is replaced by Arg; Met at position 11 is replaced by Leu; H is at position 12 is replaced by Pro; Lys at position 13 is replaced by Arg; Thr at position 14 is replaced by Asn; Pro at position 17 is replaced by Gln; Phe at position 18 is replaced by Gly; Ala at position 22 is replaced by Glu; Glu at position 25 is replaced by Asp; and Glu at position 31 is replaced by His.

Representative examples of variegin fragments are set forth in Table 1.

TABLE 1

| Peptide | Sequence |
| --- | --- |
| SEQ. ID. NO. 1 | $NH_2$-SDQGDVAEPKMHKTAPPFDFEAIPEEYLDDES-acid |
| SEQ. ID. NO. 2 | $NH_2$-SDQGDVAEPKMHKTAPPFDFEAIPEEYLD-acid |
| SEQ. ID. NO. 3 | $NH_2$-SDQGDVAEPKMHKTAPPFDFEAIPEE-acid |
| SEQ. ID. NO. 4 | $NH_2$-GDVAEPKMHKTAPPFDFEAIPEEYLDDES-acid |

Another variegin fragment that may be useful in the present invention is SDQGDVAEPKMHKTAPPFDFEAIPEEYL (SEQ ID NO:5).

Variegin fragments may also contain amino acid substitutions at one or more of the positions described above. Representative examples of such fragments include fragments having an amino acid sequence include:

```
                                          (SEQ ID NO: 6)
SDQGDVAEPAMHKTAPPFDFEAIPEEYLDDES (K10A), (SEQ ID NO: 7)
SDQADRAQPKLHRNAPQGDFEAIPDEYL, (SEQ ID NO: 8)
SDQSGRAQPKLPRNAPQGDFEAIPDEYL, (SEQ ID NO: 9)
SDQGDVAEPKMHKTAPPGDFEAIPEEYLD, (SEQ ID NO: 10)
SDQADVAEPKMHKTAPPGDFEAIPEEYLD, (SEQ ID NO: 11)
EPKMHKTAPPFDFEAIPEEYLDDES (EP25)

(SEQ ID NO: 12)
EPKMHKTAPPFDFEEIPEEYLDDES (EP25A22E)
```

-continued

EPKMHKTAPPFDFEAIPEEYL (EP21)       (SEQ ID NO: 13)

MHKTAPPFDFEAIPEEYL (MH1 8)         (SEQ ID NO: 14)

DVAEPKMHKTAPPFDFEAIPEEYL (DV24)    (SEQ ID NO: 15)
and

DVAEPRMHKTAPPFDFEAIPEEYL (DV24, K10R).  (SEQ ID NO: 16)

Thus, variants, fragments and variants of fragments typically possess at least about 50%, 55%, 60%, 65%, 70%, 75%, 80%, 85%, 90%, 95% or about 97% sequence similarity to SEQ ID NO:1.

Derivatives of variegin, and its variants and fragments may also be useful in the practice of the present invention. Representative examples of such derivatives include modified forms of variegin and its variants and fragments that are modified by the addition of sugar groups (e.g., glycosyl groups) or polymer groups (e.g., PEG) to amino acid residues in the variegin sequence. In some embodiments, the derivatives are glycosylated forms of variegin in which the Thr at position 14 of SEQ ID NO:1 is modified by a hexose moiety. Other embodiments can include other post-translational modifications known to those skilled in the art, including phosphorylation, often included on serine, threonine or tyrosine residues, sumoylation, addition various fatty acid or lipid chains, and all of these can be either alone or included in combinations. In addition, there are natural or engineered variations of amino acids that can replace residues in the sequence, such as citrulline as an uncharged analog of arginine, methyl-lysine as an uncharged analog of lysine, hydroxyproline as a structural analog of proline, among many other alternatives known to those skilled in the art.

Variegin and its analogs may be synthesized according to known procedures, e.g., peptide synthesis chemistry, including liquid and solid phase chemistry techniques. For example, peptide synthesis can be conducted via any of the solid-phase peptide synthesis (SPPS) methods (e.g., Fmoc or t-Boc chemistry approaches), all of which are well known to those skilled in the art. Typically these syntheses are performed on automated peptide synthesis instruments. In other embodiments, the peptides may be produced in microorganism or other non-human organisms genetically engineered (e.g., by transformation) with a nucleic acid that encodes variegin or its analog.

Other blood stabilization agents useful in the present invention include polysulfated disaccharides. The disaccharide component is typically lactose, trehalose, sucrose, maltose, or cellobiose. In some embodiments, the disaccharide component is sucrose or trehalose. The number of sulfate groups on the disaccharide components typically ranges from 4 to 8. Thus, embodiments include tetra-sulfated, penta-sulfated, hexa-sulfated, hepta-sulfated and octasulfated lactose, sucrose, maltose and cellobiose. See, e.g., Wall, et al., Thromb. Res. 103:325-35 (2001); Sarilla, et al., J. Biol. Chem. 285(11):8278-89 (2010). In exemplary embodiments, the polysulfated disaccharide is sucrose octasulfate (SOS) or trehalose octasulfate. The polysulfated disaccharides are indirect thrombin inhibitors, which as known in the art, are agents that act as part of an antithrombin complex and do not themselves interact directly with the thrombin active site such that they can only inactivate soluble thrombin but cannot react with fibrin-bound thrombin. SOS is known to act through heparin cofactor II, such that the SOS-HCII complex binds to and inhibits thrombin.

The blood stabilization agent may also include at least one other direct thrombin inhibitor and/or at least one other indirect thrombin inhibitor. Representative examples of direct thrombin inhibitors that may be useful in the present invention include argatroban (((2R,4R)-1-[(2S)-5-(diaminomethylideneamino)-2-[[(3R)-3-methyl-1,2,3,4-tetrahydroquinolin-8-yl]-sulfonylamino]pentanoyl]-4-methyl-piperidine-2-carboxylic acid), hirudin and its analog bivalirudin, derivatives of the pentapeptide RPPGF that contain a D-isomer and/or an unusual amino acid, e.g., rOicPaF(p-Me)—NH$_2$ (known in the art as "FM-19"), rOicPsF(p-Me), rOicPaF(p-Br), rOicPaF(p-I), rOicPaF(p-NO$_2$), F(p-Me)OicrPa, aPrOicF(p-Me), PaF(p-Me)rOic, PF(p-Me)Oicra, and PraF(p-Me)Oic (wherein the D-isomer is designated by the small case letter, and "Oic" represents the synthetic amino acid (2S,3aS, 7aS)-octahydroindol-2-carboxlic acid))) (e.g., Nieman et al., J. Thrombosis Haemostasis 6:837-845 (2008)), aprotinin, a peptide with known thrombin inhibition potential (e.g., Pintigny et al., Eur. J. Biochem. 207:89-95 (1992)), and D-phenylalanyl-L-prolyl-L-arginine chloromethyl ketone (PPACK), known as a heparin alternative (e.g., Lyon et al., Clin. Chem. 41:1038-1041 (1995)).

Representative examples of indirect thrombin inhibitors that may be useful in the present invention include heparin in its various forms defined by molecular weight distribution of the specific preparation (e.g., unfractionated, low molecular weight (typically a 3-7 kilodalton fraction), ultra-low molecular weight (typically a 2-3 kilodalton), and similar size-specific subfractions). Therapeutic subfractions of heparin, isolated via different defractionation methods based either on size or various chemical extraction processes, include dalteparin, enoxaparin, adreparin, parnaparin, reviparin, tinzaparin, bioparin, miniparin, sandoparin, semuloparin, and nadroparin and other similar molecules.

The mode of purification may depend upon the method of synthesis. In general, the purity of the blood stabilizing agent will vary depending on the agent used and its source. In general, the purity of the platelet stabilizing agent is at least about 70%, 75%, 80%, 85%, 90% or 95%, or even higher.

The blood stabilization agent is present in the collection device in an effective amount to preserve laboratory-testable function of blood and its components. For example, in the case of platelets, the amount is effective to preserve platelet function which may include their ability to aggregate, and to avoid or inhibit platelet degranulation that occurs when platelets are not preserved and thus lose their native granulated state, and/or to stabilize one or more endogenous proteins that may be present in a plasma portion of the of the blood or blood sample or composition containing a blood component. The choice of specific blood stabilization agent and the amount or concentration to include in the device depend on several factors including the nature of the sample, the potency of each agent and its solubility in water, the amount of time blood stabilization is desired, the volume of the blood collection device, the extent of hemolysis caused by the addition of the agent to the sample, and the nature and extent of non-specific interactions (e.g., due to presence of other proteins in blood such as serum albumin). Accordingly, for purposes of the present invention, the amount of the blood stabilization agent(s) that may be present is more conveniently expressed in terms of a range of concentration (from which the actual amount of the agent can be easily calculated).

With respect to platelets, the preservation of function means that the platelets are maintained after collection and prior to analysis in a state in which they can be activated or reactivated such that platelet aggregation (as a measure of platelet function) may be measured in vitro. Activated or reactivated, as used herein in the context of platelets, means that the ability of the platelets to initiate a platelet binding cascade and aggregate are preserved for in vitro analysis in a laboratory, but that platelet aggregation is inhibited from being induced as an artifact of collection, transport, and storage in typical blood collection devices for in vitro diagnostic procedures.

For example, some blood stabilizing agents are more potent than others, and thus will require a smaller concentration per ml of sample, depending on the utility. Different amounts of blood stabilizing agents may be needed to stabilize blood components such as platelets that may be present in an enriched composition (such as PRP) as compared to the same volume of a whole blood sample (e.g., which would contain fewer components such as platelets per unit volume).

In general, the at least one blood stabilizing agent may be selected to achieve at least about 50% aggregation inhibition activity at room temperature, preferably in the range of at least about 60% to about 75% inhibitory activity, and more preferably at least about 75% inhibitory activity, over the course of collection, and storage and/or transport, up to the time of analytical testing or therapeutic use. Depending upon the need, stabilization may be achieved for at least 1 hour up to about 6, 12, 24, 36, 48, 60, 72, 84, 96 hours or more.

Skilled practitioners will appreciate the hemolyzed samples are an obvious visual clue that damage to blood cells has occurred, either during the collection, transport, or storage of blood samples. Although hemolysis is not necessarily detrimental to any one clinical assay, it is a well known interference for some tests, and thus it is preferable to avoid causing hemolysis. Hemolysis can be measured by visual scale (e.g., mild or slightly pink, moderate or noticeably red, or severe or dark red). Hemolysis can also be measured by spectroscopic measurement of the red color of the hemoglobin itself, and can be reported by the concentration of hemoglobin released into the serum or plasma (e.g., such that less than about 20 mg/dL concentration of released hemoglobin, or to an extent that the hemoglobin concentration cannot be measured visually or by spectroscopy represents "minor or negligible" hemolysis, about 20 to about 100 mg/dL represents "mild" hemolysis, about 100 to about 300 represents "moderate" hemolysis, or greater than about 300 mg/dL represents "severe" hemolysis).

With the foregoing in mind, the concentration of blood stabilization agent generally ranges from about 100 nm to about 50 mM, and in some embodiments from about 1 µm to about 10 mM, and in some embodiments from about 5 µm to about 5 mM, and in some embodiments from about 20 µm to about 3 mM, and in some embodiments from about 50 µm to about 2 mM.

For example, the concentration of variegin or its analog generally ranges from about 1 µM to about 10 mM. In other embodiments, the concentration of blood stabilizing agent ranges from about 1 µM to about 10 mM. In yet other embodiments, the concentration of variegin or its analog ranges from about 10 µM to about 1 mM. In yet further embodiments, the concentration of variegin or its analog ranges from about 25 µM to about 500 µM. In other embodiments, the concentration of variegin or its analog ranges from about 50 µM to about 300 µM. In even yet further embodiments, the concentration of blood stabilizing agent is about 150 µM, and in other embodiments is about 300 µM.

The concentration of polysulfated disaccharide generally ranges from about 50 µM to about 50 mM. In other embodiments, the concentration of polysulfated disaccharide ranges from about 250 uM to about 25 mM. In yet other embodiments, the concentration of polysulfated disaccharide ranges from about 1 mM to about 5 mM, and in yet other embodiments, from about 2 mM to about 3 mM. In yet further embodiments, the concentration of polysulfated disaccharide is about 2 mM, and in other embodiments is about 3 mM. All subranges within these ranges are also contemplated. The term "about" as used in connection with all concentration values disclosed herein refers to variability (plus/minus value) of 50%.

The blood stabilizing agent may be in any suitable form including a solution, suspension or other liquid, a pellet, a tablet, a capsule, a spray-dried material, a freeze-dried material, a powder, a particle, a gel, crystals or a lyophilized material. The blood stabilizing agent is preferably introduced into the reservoir of the container in such a form so as to optimize the shelf life of the agent, i.e., to prevent degradation of the blood stabilizing agent which would result in reduced efficacy. Providing the agent in dried e.g., lyophilized, form is advantageous in that it provides good stability and also allows subsequent sterilization, both of which are key from a standpoint of automation and standardization. In addition to being disposed in the reservoir, the blood stabilizing agent may be located on any surface of the device. The stabilizing agent may also be disposed on the interior wall, on stoppers and seals for closing such devices or on mechanical, or other inserts placed within such devices.

In addition to the blood stabilizing agent, the device of the present invention may also contain an anti-coagulant. Clotting of the sample does not necessarily adversely impede measurement of platelet aggregation, but formation of too much insoluble material eventually prevents access to enough of the liquid sample to test. Completely clotted samples are useless for platelet studies. As such, avoiding formation of insoluble material is a preferable attribute of a blood sample intended for blood function testing. The anti-coagulant may increase the anti-coagulation, blood stabilizing and/or anti-hemolytic effects provided by variegin and/or the polysulfated disaccharide. Representative examples of anti-coagulants that may be useful in the present invention include coagulation Factor Xa inhibitors, Factor VII inhibitors, Factor IX inhibitors, Factor XII inhibitors, and other thrombin (Factor II) inhibitors. Several representative examples of Factor Xa inhibitors are described in Qiao et al., Bioorg. Med. Chem. Lett. 19:462-468 (2009), the structures of two of which are as follows:

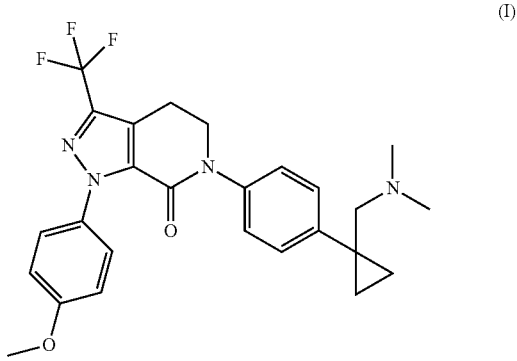

(I)

-continued

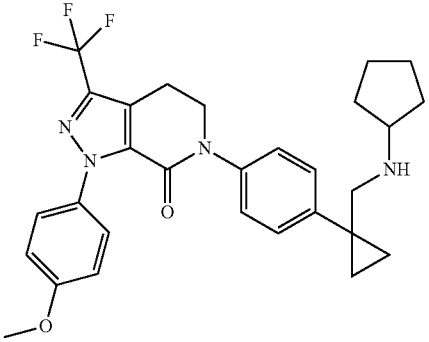

(II)

I=6-(4-{1-[(dimethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one; II=1-(4-methoxyphenyl)-6-[4-[1-(pyrrolidin-1-ylmethyl)cyclopropyl]phenyl]-3-(trifluoromethyl)-4,5-dihydropyrazolo[3,4-c]pyridin-7-one. Amounts of these particular anti-coagulants generally range from 100 µg/ml to 25 mg/ml, and in some embodiments from about 1 mg/ml to about 10 mg/ml.

In some embodiments, the additional anticoagulant agent is argatroban and its derivatives (e.g., Tamura et al., Circ. J. 73(3):540-8 (2009) and Kalb et al., Platelets 20(1):7-11 (2009)). Concentration of argatroban generally ranges from about 1 µM to about 2 mM, and in some embodiments from about 10 µM to about 1 mM, and in yet other embodiments from about 25 µM to about 100 µM.

In other embodiments, the additional anticoagulant is antistasin or an antistasin-related peptide (a peptide fragment derived from antistasin protein) (see Ohta et al., Thromb Haemost. 72(6):825-30 (1994)). Concentration of antistasin generally ranges from 100 nM to about 2 mM, and in some embodiments from about 1 µM to about 100 µM.

Examples of yet other anticoagulants that may be useful in the present invention include Antithrombin III (Jorgensen et al., Biochem. J. 231(1):59-63 (1985)) and E-76, which is a peptide derived from phage library selection against the tissue factor-VIIa complex (Dennis et al., Nature 404(6777): 465-70 (2000)).

The devices of the present invention may also include carrier media (e.g., water or alcohol), stabilizing media (polyvinylpyrollidone, trehalose, mannitol, etc.) and/or one or more other additives for treating the blood or blood sample. Suitable additives include phenol, phenol/chloroform mixtures, alcohols, aldehydes, ketones, organic acids, salts of organic acids, alkali metal salts of halides, organic chelating agents, fluorescent dyes, antibodies, binding agents (not chelating agents), buffering agents, and any other reagent or combination of reagents normally used to treat biological samples for analysis.

The additives and/or anticoagulants may be disposed in the reservoir and/or elsewhere in the device provided that they come into contact with the sample in order to provide their intended effect. For example, these ingredients may also be disposed on the interior wall, on stoppers and seals for closing such devices or on mechanical or other inserts placed within such devices.

The methods of the present invention include introducing blood or a blood sample, into the device containing the blood stabilizing agent. In some embodiments, the blood sample is withdrawn from the patient directly into the container without any intervening process steps. In other embodiments, the collected sample is further processed to prepare a composition such as an enriched composition containing a blood component such as PRP.

The sample may then be subjected to an analytical e.g., diagnostic, test to measure a parameter of blood. In some embodiments, the parameter that is measured is platelet function, which can be assessed by the ability of the platelets contained in the sample to aggregate upon stimulation. Such a test may also be performed even if the sample (e.g., PRP) is intended for therapeutic use.

There are several in vitro diagnostic tests that can be applied to analyze platelet function in drawn blood samples and compositions containing platelets. Light transmission aggregometry (LTA) is a widely used technique. LTA relies on measuring the amount of light that can pass through a preparation of platelet-rich plasma (PRP). In LTA, the high number of platelets in the PRP scatters photons, but upon aggregation stimulated by addition of a platelet agonist, the platelets clump into masses which eventually become so large that the fall to the bottom of the test chamber. Throughout the process, the light scattering is reduced, and aggregation is measured as an increase in the amount of light that can pass through the sample. Another method is whole blood impedance aggregometry (WBIA), as is described in Example 1 below. Another relevant technique is embodied in the VerifyNow System sold by Accumetrics, which uses a variation of aggregation measurements which relies on the platelets aggregating onto the surface of fibrinogen-coated latex beads, and aggregation is monitored by absorbance changes in the signal. An instrument called PFA-100, marketed by Siemens, measures platelet function by analyzing the time required for thrombus formation in a model system. PFA-100 uses a cartridge having a small aperture through which blood can be pulled, and this aperture is occluded when platelet aggregation is induced, and the force required to draw blood through the aperture increases as a function of aggregation. PFA-100 represents a "physical" method in which a macromolecular outcome of platelet function is measured, in this case occlusion of an aperture in a device. Another physical method is thromboelastography, in which clot formation, including aggregation of platelets as an integral part of the clot mass, is measured by the amount of physical drag upon a moving pin dipped into the sample, with the drag increasing as the clot mass increases. By contrast, flow cytometric measurements that can be made directly on individual platelet cells, in which specific molecular changes in the cells can be measured. Using flow cytoometry, many specific changes that occur upon platelet activation can be measured, sometimes even as precursors to the more physical characterization of aggregation in the above measurements, such as changes in the shape and orientation of surface proteins including cell surface receptor proteins, or changes in the ionic content of platelets (e.g., a change in concentration of intracellular calcium is know to happen upon platelet activation). Further, the vasodilator-stimulated phosphoprotein (VASP), a phosphorylated protein inside platelets, becomes less phosphorylated upon activation of the P2Y12 receptor on the platelet surface, and thus a drop in VASP phosphorylation, which can be monitored by flow cytometry, is indicative of platelet activation (see, for example, Geiger et al (2005) Clin. Chem. 51(6): 957-965). While the phosphorylation state of VASP can be measured inside platelets using flow cytometry, indirect methods using more typical immunochemistry methods to do the same have also been described.

As illustrated in the working examples, the ability and extent of platelets to aggregate can also be measured by performing "aggregometry" on blood samples. Aggregometry may be measured as "whole blood impedance aggregometry" (WBIA), among the several ways of performing aggregometry. An advantage of WBIA is that while LTA requires preparation of PRP as the test sample, WBIA can work on a whole blood sample but can also work with PRP. In WBIA, two wires inside a special sample cup are submerged in a prepared blood sample, with a very small gap between the wires, and a small electrical current is run between the wires (the current is conducted through the blood in the small gap). Upon chemical stimulation introduced by the operator, platelet aggregation is initiated. The platelets preferentially accumulate on the surfaces of the wires as they aggregate, and the increasing build-up of platelets begins to insulate against the electrical current, causing an increase in electrical impedance, which is recorded by the instrument. A typical experiment collects electrical current data for 6 minutes after introduction of the chemical stimulant.

These measurements are intended to be sensitive to the extent of platelet aggregation (also referred to, in this case, as platelet function), and also to some extent simply to the number of platelets in the sample. In some embodiments, it may be beneficial to induce platelet aggregation at a specific time after collection. Thus, a platelet agonist may be added to the sample to induce aggregation. Agonists are generally known to those skilled in the art, and can include, for example, collagen, adenosine diphosphate (ADP), arachadonic acid (AA), epinephrine, thrombin receptor activator peptide (TRAP), collagen-related peptide (CRP), ristocetin, thrombin (and thrombin analogs), thromboxane receptor agonists (e.g., U46619), cationic propyl gallate, and convulxin. In many cases, the agonists of most interest are drugs designed to prevent unhealthy build-up of platelet aggregates, as will be described in more detail in some of the examples that follow.

There are also a number of antagonists, or compounds that can inhibit platelet response and their effects can also be measured. By mode of action, these compounds, known to those skilled in the art, include cyclooxygenase inhibitors (e.g., acetylsalicylic acid (ASA, or "aspirin")), thromboxane receptor inhibitors (e.g., terutoban, sulotroban, ifetroban), thrombin receptor antagonists (PAR-1, vorapaxar, atopaxar), GpIIbIIIa receptor inhibitors (e.g., abciximab, tirofiban, eptifibatide), P2Y12 receptor antagonists (e.g., clopidogrel (trade-name Plavix), [dichloro-[[[(2R,3S,4R,5R)-3,4-dihydroxy-5-[6-(2-methylsulfanylethylamino)-2-(3,3,3-trifluoropropylsulfanyl)purin-9-yl]oxolan-2-yl]methoxy-hydroxyphosphoryl]oxy-hydroxyphosphoryl]methyl]phosphonic acid (Cangrelor), or (1S,2S,3R,5S)-3-[7-[(1R,2S)-2-(3,4-Difluorophenyl)cyclopropylamino]-5-(propylthio)-3H-[1,2,3] triazolo[4,5-d]pyrimidin-3-yl]-5-(2-hydroxyethoxy)cyclopentane-1,2-diol (Ticagrelor), and other compounds that can disrupt biochemical function of platelets.

It is advantageous to stabilize drawn blood samples and its components for a wide variety of diagnostic testing as well as for subsequent therapeutic use. The following disclosure illustrates representative examples of these utilities, particularly in the context of preserving platelet function.

Given the acute nature of adverse cardiovascular events, it can be critical to know that the first therapeutic approach selected for a patient will have immediate benefit, ideally without having to monitor patients and select alternative therapies. Thus, before patients undergo such therapy, they may have blood samples drawn and tested for platelet function. Such testing may also be recommended for on-going monitoring of the effect of the prescribed anti-thrombotics, testing for either over-inhibition or under-inhibition of platelet function. Similar testing is often employed for pre-surgical screening to rule out potential adverse bleeding effects during surgery/recovery. Importantly, the testing can be inaccurate if the function of the platelets is not stabilized in the drawn blood sample, either allowing them to aggregate prior to testing (e.g., no function "left" to test for), or perhaps to "die" or otherwise lose natural function prior to testing.

For example, antiplatelet drugs have a very high usage in the United States and worldwide. Taking a "baby" aspirin daily for heart health has become a common practice, with as many as 50 million Americans taking a daily aspirin dose. Plavix (or clopidogrel, by chemical name), is a widely used antiplatelet therapy, used in both acute settings (e.g., immediately after interventional cardiology procedures or in emergency situations concerning heart attack or stroke) and for chronic care of patients who have had cardiopulmonary or circulatory complications. The mechanism of action of Plavix and aspirin ultimately inhibits platelet aggregation, which is intended, for example, to reduce the likelihood of arterial blockage from spontaneously formed platelet aggregates that can lead to heart attack or stroke. There are over 29 million prescriptions written annually for Plavix. These drugs function by blocking chemical pathways that induce platelets to aggregate, and thus can help mitigate dangerous cardiovascular events which can be exacerbated by platelet aggregates (thrombi) mechanically occluding arterial or venous blood flow. Perhaps as many as 50 percent of humans do not respond well to these drugs—and a topic which has been of increasing interest in current medical and scientific literature (e.g., Tentzeris et al., Thromb Haemost. 105 Suppl 1:S60-6 (2011)). Patients who are "resistant" to these drugs do not experience this platelet inhibition, and thus are at very high risk of adverse events. The first or only indication that these drugs have not worked as intended may occur when the patient actually experiences the heart attack or stroke that the prescription was intended to prevent.

Much like Plavix and aspirin, platelet inhibitors (agonists) that mimic these effects can be added to a drawn blood sample to test for efficacy without necessarily requiring patients to take the drug (prior to blood draw). As described above, an agonist can be added which mimics the various chemical signals that might be induced inside the body upon damage to the vasculature, and the effects of platelet antagonists can be tested for their ability to mute the response to the agonists.

In particular, aspirin immediately inhibits platelet function, so simply adding a small amount of aspirin directly to a blood sample before analyzing platelet aggregation may allow for a determination of whether aspirin would be beneficial. Some of the P2Y12 inhibitors, such as cangrelor and ticagrelor, also can bind directly to and inhibit platelets, and thus can be added directly into a blood sample prior to testing for their efficacy as platelet inhibitors.

On the other hand, since Plavix is a "pro-drug" which must be converted into an active form by metabolic processing after it is ingested. Pro-drugs are often processed by enzymes in the liver, resulting in active forms that can then circulate in the blood. As such, adding the ingested (pro-drug) form of Plavix to a drawn blood sample will not result in inhibition of platelet aggregation. However, the actions of Plavix can still be mimicked to allow for testing without the patient first having to actually take the drug. Plavix and other similar drugs act to inhibit the pathway that allows ADP to stimulate, or agonize, platelets. The chemical 2-Methylthioadenosine 5'-monophosphate (2MeSAMP), inhibits the same targets that Plavix and other P2Y12 inhibitors inhibit in vivo (Srinivasan et al., J. Biol. Chem. 284(24):16108-17 (2009)), but can act directly on platelets, and so can be added to a blood sample immediately prior to testing. Thus, adding a platelet antagonist such as 2MeSAMP to a drawn blood sample prior to testing platelet aggregation allows for a determination of whether Plavix would be therapeutically useful in a patient. The antagonist 2MeSAMP also provides an adequate mimic for the effects of the drugs Cangrelor and Ticagrelor.

Platelet function testing may thus provide a direct way to measure whether or not these drugs have had their desired effect on the patient, by, for example, drawing blood and testing platelet function before and after initiating drug therapy. If the patient is properly responding to the drugs, the measured platelet function would decrease after dosing. Ongoing monitoring of patients on long-term therapy can also be conducted to ensure platelet function is being inhibited to a level sufficient to help prevent heart attack or stroke, while at the same time ensuring that platelet function has not been overly inhibited. In this latter case, there would be a much higher risk of the patient experiencing unstoppable bleeding events (e.g., a drug-induced haemophilia-like state).

A related use for these tests is in the context of pre-surgical screening. Testing of inherent platelet function in patients prior to surgery may identify those patients predisposed to adverse bleeding events, so that surgery could be postponed or the condition could be treated prior to the surgery (see, for example, Bracey et al., Am. J. Cardiol. 98(10A):25N-32N (2006)). For example, patients would be identified as "at risk" if their inherent platelet aggregation potential was abnormally low, as judged by aggregometry tests.

Platelet function may also be preserved for purposes of protein or metabolite biomarker testing. Platelets contain proteins and metabolites of diagnostic interest, but the assay value is more likely to be in measuring the concentration of the freely circulating forms of these biomarkers in plasma. It is believed that degranulation of platelets, especially upon platelet activation or aggregation, can lead to artificially elevated levels of these markers and represents a pre-analytical error if not controlled. Similarly, the platelet granules also contain enzymes which can damage these circulating biomarkers, and thus result in artificially low levels of the biomarkers of interest. Although certain inhibitors could be included in a blood collection tube to "intercept" any enzymes that evolve from activated platelets, it is desirable to simply prevent platelet activation in the first place by providing stabilized platelets for testing of these plasma-borne biomarkers.

Yet another use of the present invention pertains to use of the stabilized platelets for use in certain therapeutic applications. Autologous platelet gel therapy is a process for the treatment of certain wounds and a wide range of other conditions ranging from dental implant healing to injections intended to repair ligament damage. The premise involves drawing a plasma sample, isolating "platelet rich plasma" and then reintroducing the preparation into the patient at the site where healing is desired. One method involves adding thrombin, or another coagulant, to induce clotting, resulting in a "glue" which forms quickly and can be applied into position to improve healing. Platelet degranulation, which will release cytokines and certain growth factors, is believed to stimulate wound healing in this autologous therapy approach. If platelet function is lost and as a result, platelets become prematurely activated, they may lose this therapeutic effect. Collecting and/or storing platelets in the presence of the blood stabilization agents of the present invention are thus advantageous from this standpoint as well.

In addition to platelet function analyses, other clinically relevant blood parameters may be measured. Representative blood parameters include measurements of plasma-borne analytes such as are commonly tested in clinical chemistry, immunochemistry, enzymology, and other measurements of molecules "outside" of the cells (in the plasma portion of blood). Other blood parameters include cell analyses, such as hematology, complete blood count (CBC), blood films and microscopic analysis of blood cells, platelet granulation/degranulation measurements, and biochemical and metabolic characterization of cells (often measured by, for example, flow cytometry, molecular biology, proteomics). The blood and blood samples stabilized of the present invention with these agents will be compatible and thus useful with any standard clinical assay in which anticoagulation is a base requirement of the blood sample. For example, standard clinical hematology tests such as complete blood count (CBC), in which the various cells in a blood sample are distinguished and counted, rely on an anticoagulated sample, so that all of the cells stay in the suspended/dissolved whole blood state. Commonly, for routine CBC purposes, blood is stabilized using EDTA. Any tests done on plasma obviously require anticoagulation (or the sample would clot, and would then be defined as serum). Traditional clinical chemistry measurements (a menu of some tens to hundreds of typical analytes well-known to those skilled in the art) are often done with heparin-anticoagulated plasma samples. Similarly, immunochemistry, or quantification of analytes via the use of antibody binding as the detection mechanism, also relies on plasma samples. However, EDTA and typically used concentrations of heparin (e.g., 13 U/ml) both interfere with the actual ability to perform platelet function testing. As such there is no reciprocity of the cross-platform applicability of samples. The present invention overcomes this limitation in that it stabilizes blood samples for platelet function testing as well as these other common clinical hematological tests.

To facilitate use of the present invention, one or more of the devices may be packaged in the form of a kit. In some embodiments, the kit will include one or a plurality of devices, e.g., arranged in open racks or in a sealed package. The kits may also contain one or more elements that are useful drawing and collecting blood, e.g., needles, tourniquets, bandages, alcohol and wipes, and lancets. Kits may also include other types of blood collection devices such as tubes, that have disposed therein known blood stabilization agents and/or anti-coagulants, examples of which include EDTA tubes (e.g., for routine hematology counts), heparin tubes (for clinical chemistry), citrate tubes (for coagulation testing), and other specialty tubes (for use in proteomics, genomics, and the like). The kits of the present invention may also include instructions for use.

In some other embodiments, the kit may include a primary collection device, e.g., a plasma tube with a plasma separating tube having a separating element therein, and a secondary tube for testing, e.g., for pouring or otherwise dispensing the collected plasma. The separating element in the primary tube may be of an appropriate density to enable isolation of platelet-rich plasma from the other cellular content of the blood. The secondary testing tube may be of the same or different size than the primary tube, depending on the desired testing. Both tubes may have a platelet stabilizing agent disposed therein. The kit may further include a tube-to-tube transfer device to prevent the need for pouring or other unsafe transfer practices, in which case the secondary tube would be at a reduced pressure to draw in the plasma.

In another aspect of the invention, a platelet antagonist can be included in the primary blood collection tube, along with the blood stabilization agent. Testing the platelet function of such a sample, by stimulating with an appropriate agonist as part of an in vitro diagnostic assay, may directly reflect the efficacy of the antagonist/drug on that patient's blood. In a preferred embodiment, a kit may contain at least two tubes, in which one tube contains the blood stabilization agent, and another tube contains the blood stabilization agent and the platelet antagonist, thus allowing the operator to measure platelets in both the inhibited and uninhibited states without having to perform any other manipulation of the blood samples prior to performing the aggregation assay.

The invention will now be described in terms of the following non-limiting examples.

EXAMPLE 1

Extended Stability of a Whole Blood Sample for Platelet Function Testing, as Reflected by Platelet Aggregation Measurements Blood samples: Venous blood was drawn from a human subject into tubes containing either sodium citrate (3.2%) or 150 µM variegin (SEQ ID NO:1). The blood was allowed to stand at room temperature, in undisturbed aliquots, until tested at the times indicated. Samples were inverted several times immediately prior to testing, to re-suspend blood cells that naturally settle over time.

Measurements: Testing of platelet function (which in this experiment, was aggregation activity) was done using the Multiplate instrument (Verum Diagnostics, Munich, Germany), which uses whole blood as the sample and an increase in impedance as the measurement of platelet aggregation. The instrument was used per manufacturer's instructions. Briefly, 300 microliters of isotonic saline was warmed in each reaction cuvette, and to this was added 300 microliters of the whole blood sample. In reactions where aspirin or other platelet antagonists (inhibitors) were added in vitro, 20 microliters (µL) of a stock solution of aspirin was spiked into the samples. The aggregation reaction was initiated by addition of a platelet agonist, in this case collagen, at 3.2 µg/ml and volume (20 µl) per manufacturer's instructions. Upon addition of the collagen, the impedance measurements began automatically, and were continued for 6 minutes, representing the full course along the x-axis in the graphs shown in FIG. 2. The graphs show platelet aggregation, as reported by impedance, as an arbitrary unitless measurement on the y-axis, over the 6-minute run time on the x-axis. Traces shown are raw platelet aggregation data delivered from the instrument. The duplicate traces evident in some of the graphs represent two duplicate measurement channels that always ran simultaneously, to assist with statistical significance of the data, and often so closely overlap as to look like only a single trace in some graphs. Representative data are shown for blood that dwells at room temperature after the initial draw for 1 hr, 24 hr, 48 hr, and 72 hr. Data are shown for the blood itself, as well for blood pre-treated with aspirin to inhibit platelet function immediately prior to testing.

Figure 2:
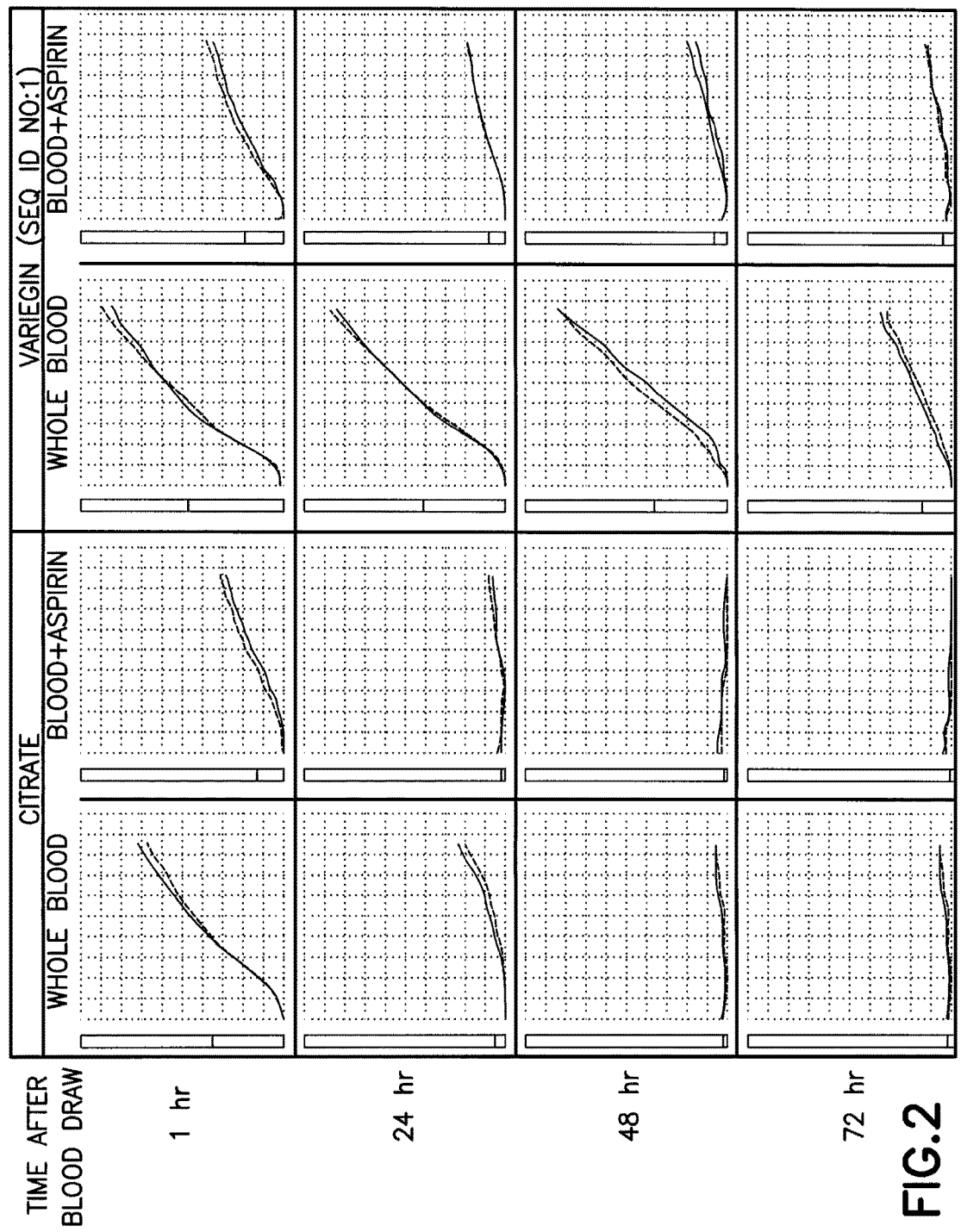
FIG. 2 shows a series of graphs plotting platelet aggregation in an inventive embodiment versus a comparative non-inventive embodiment, as measured by impedance, as an arbitrary unitless measurement on the y-axis, as a function of 6 minutes of run time (after the introduction of a platelet stimulant) on the x-axis.

According to diagnostic regulatory bodies such as the Clinical Laboratory Standards Institute (CLSI), citrated whole blood is considered the clinical standard for use in platelet function testing. Thus, we compared the inventive embodiment against citrate. As shown in FIG. 2, the citrate and inventive samples when fresh, at one hour, functioned quite similarly. Both responded strongly to collagen and showed measureable antagonism by aspirin. However, the strength of the signal for the inventive embodiment was higher than the citrate reference sample, even in the "fresh" sample, demonstrating the advantages of the present invention for testing even within the current clinical guidelines which recommend testing of citrated blood within a maximum of 2-4 hours after blood draw. The immediate exposure of blood to the chemistry of the invention has a measureable benefit. At all longer times, it is clear that the citrate blood signal was clearly lost, resulting in almost non-measureable signal, and thus making any observation of a further decrease by aspirin antagonism essentially impossible. By contrast, at 24 and 48 hrs, the inventive embodiment preserved platelet function substantially at the level of function measured in the 1 hr-old sample, and also preserving the ability to measure aspirin antagonism. At 72 hr, the signal was slightly reduced but still sufficiently strong to still allow observation of further decrease when having added aspirin. Thus the results of this experiment demonstrate both beneficial aspects of the present invention, namely a stronger platelet function signal with fresh samples as well as a greatly preserved platelet function up to several days after drawing, while also allowing the blood to be stored simply at room temperature.

EXAMPLE 2

Figure 3:
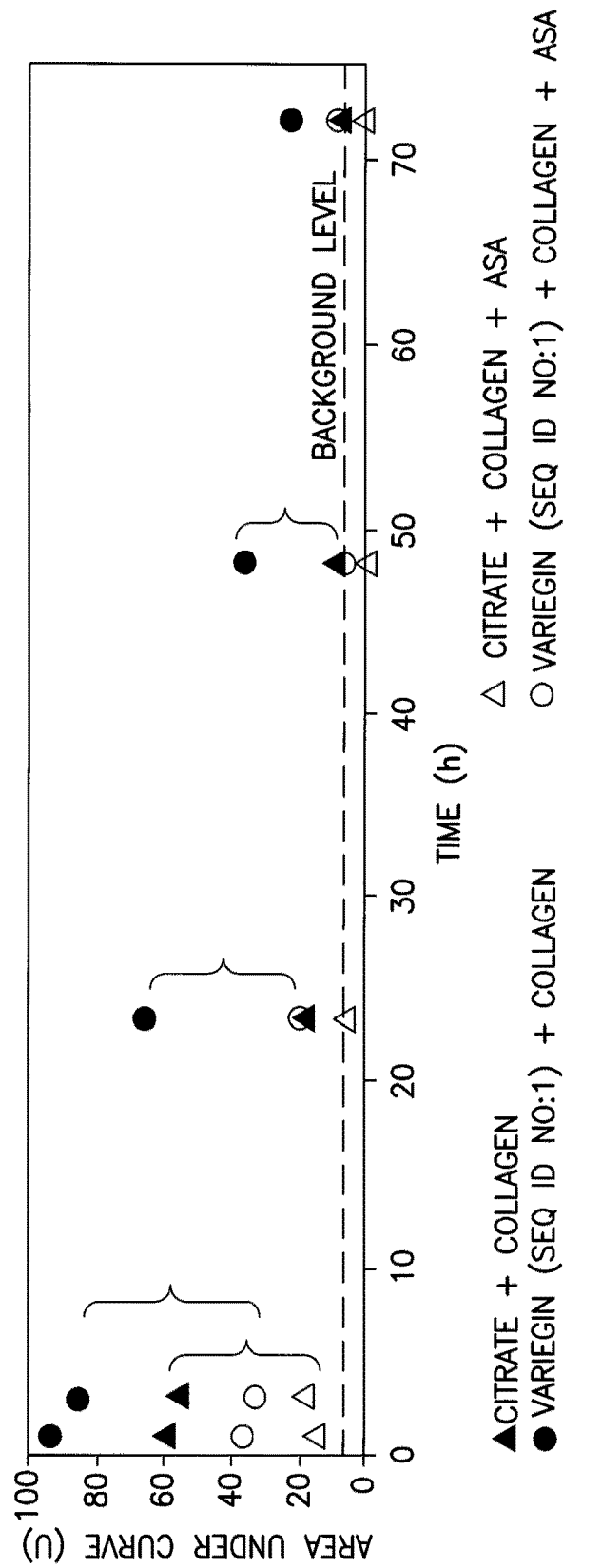
FIG. 3 is a graph showing platelet aggregation (measured as area under the curve (AUC)) as a function of time in blood samples collected in an inventive embodiment containing variegin (SEQ ID NO:1), in combination with the assays using the platelet agonist collagen with or without the platelet antagonist acetylsalicylic acid (ASA, or aspirin), as compared to non-inventive devices containing citrate, and collagen with and without ASA.

Extending Usable Time of a Drawn Blood Sample for Platelet Function Measurements FIG. 3 illustrates the limitations of platelet function measurement methods, and how loss of function after a sample is drawn adversely affects the ability to generate useful clinical diagnostic data. The experiments were performed as described in Example 1. In this case, the data are plotted as a function of time that the blood sample dwells outside of the body (x-axis) versus platelet function as shown as the area under the curve (AUC) as one representation of the platelet aggregation signal. AUC is the integrated signal from the raw data traces shown in Example 1, and also is reported as a unitless measurement. The effective background level of the instrument is drawn as a dashed line across the bottom of the graph. Any AUC measurement of aggregation at or below this level was considered so weak as to be unreportable, essentially representing a "null" data level.

At 24 hr, it became evident that the platelets in the citrated blood sample lost sufficient function as to be very close to the effective null level, and in the presence of aspirin had already reached this null level. By 48 hr, even in the absence of added aspirin, no meaningful aggregation was detected for the citrated sample. By comparison, the inventive embodiment stabilized platelet function allowing for meaningful measurements even at 72 hr after blood draw.

Figure 4:
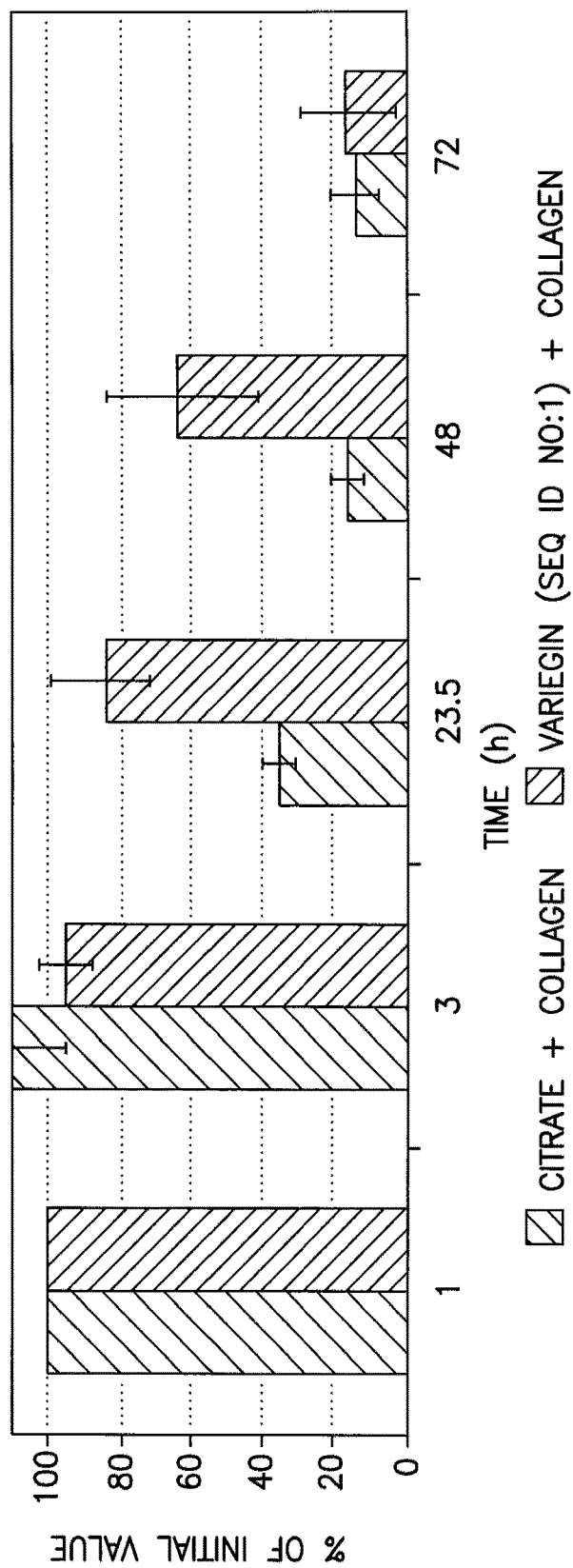
FIG. 4 is a bar graph that shows platelet aggregation (measured in terms of percent of initial value) as a function of time, in blood samples collected in an inventive embodiment containing variegin (SEQ ID NO:1), in combination with collagen used as the platelet agonist, as compared to a non-inventive device containing citrate and collagen.

Yet another view of the data is represented in FIG. 4, in which the platelet aggregation measured for each type of sample is reported as a percentage relative to the aggregation measured for the 1 hr sample. Data in this graph are reported as a average of three human subjects, with the error bars representing one standard deviation from the average. In this view, the data show that within 24 hr, platelets collected and stored with citrate lost well more than half of their function, and by 48 hr, lost more than 80% of function. By comparison, as of 48 hr, well more than half of the signal was maintained for platelets collected and stored with the inventive embodiment.

EXAMPLE 3

Effect of Various Concentrations of Variegin on Platelet Function Preservation and Anticoagulation Relative stability of platelets was examined with respect to a range of concentrations of variegin (SEQ ID NO:1). Experiments were performed as described above, using either collagen or adenosine diphosphate (ADP) as agonists, all per manufacturer's recommended protocols. Table 2 lists a qualitative assessment of stability, namely how long after initially drawing the blood was platelet aggregation measureable above the effective instrument baseline, the time to first visual observation of clotted, insoluble material in the whole blood sample, and an assessment of the severity or extent of the presence of this insoluble material was also recorded.

TABLE 2

Effect of various concentrations of variegin (SEQ ID NO: 1) on platelet stability and blood sample quality.

| Inventive embodiment | Time after blood draw where aggregation was still measurable above baseline | Visual inspection for insoluble material |
|---|---|---|
| 150 µM variegin | 72 h or longer | Trace at 48-72 h. Solid clots by 96 h |
| 75 µM variegin | 48-72 h | Trace clots by 32 h |
| 50 µM variegin | 24 h | Moderate at 24 h, extensively clotted by 48 h |
| 15 µM variegin | 24 h | Moderate at 24 h, clotted by 48 h |
| 2 µM variegin | 2 h | Solid clots at 7 h |

The results show that increases in concentrations of variegin resulted in longer overall function preservation (stabilization) effect, both in terms of having measurable platelet aggregation signals and the delay in appearance of insoluble material in the whole blood sample.

The results also show that the use of the present invention can be customized and suited to specific use requirements. For example, in a situation where a sample may need to be collected and tested rapidly, such as in a hospital emergency department, it is possible to achieve several hours of stability by using relatively low concentrations (e.g., 2 µM) of the blood stabilization agent such as variegin. When longer stabilization times are necessary, such as in situations where testing will be done possibly several days after collection, the results show that using relatively higher concentrations (e.g., 150 µM) of the blood stabilization agent such as variegin is beneficial. In conjunction with the benefits of the present invention over citrate, the present invention may provide advantages of stronger platelet aggregation signal across a range of timeframes by selection of an appropriate concentration of the blood stabilization agent.

EXAMPLE 4

Effect of Variegin and Other Variations of the Variegin Peptide on Platelet Function Preservation and Other Aspects of Sample Quality Experiments were performed testing several analogs of variegin (SEQ ID NO:1). Table 3 lists the peptides that were tested, all of which were produced by typical solid-phase synthesis.

TABLE 3 sequences of variegin and variants

| Peptide | Sequence number | Sequence |
|---|---|---|
| Variegin (full 32 residue length) | 1 | SDQGDVAEPKMHKTAPPFDFEAIPEE YLDDES |
| Variegin Nt29* | 2 | SDQGDVAEPKMHKTAPPFDFEAIPEE YLD |
| Variegin Nt26 | 3 | SDQGDVAEPKMHKTAPPFDFEAIPEE |
| Variegin Ct29 | 4 | GDVAEPKMHKTAPPFDFEAIPEEYLD DES |
| Variegin Ct22 | 17 | MHKTAPPFDFEAIPEEYLDDES |
| Variegin K10A | 6 | SDQGDVAEPAMHKTAPPFDFEAIPEE YLDDES |

Nomenclature: Nt abbreviation represents amino-terminal amino acids, with number representing the count of residues starting at the amino-terminus. Ct represents all carboxy-terminal amino acids, similarly numbered from amino-terminus. K10A is a single residue variant, per standard protein sequence nomenclature.

These peptides were used as the blood stabilization agent, and were spiked into blood immediately after collection into an empty, evacuated blood collection tube, achieving a final concentration of 150 µM. The blood was allowed to dwell in a whole-blood state at room temperature, until assayed for platelet aggregation potential, all as described in Example 1. Agonists used included collagen and ADP, following manufacturer's instructions. Table 4 lists a qualitative assessment of stability, namely how long after initially drawing the sample was platelet aggregation measureable above the effective instrument baseline. Additionally, the time to first visual observation of clotted, insoluble material in the whole blood sample, and an assessment of the severity or extent of the presence of this insoluble material was also recorded. In some cases, only visual characterization of the amount of insoluble material was reported, without having performed any platelet aggregation measurements.

TABLE 4

Variants of variegin, and their effect on preservation of platelet function and sample solubility (anticoagulation) stability.

| Peptide, concentration | Time after blood draw where aggregation was still measurable above baseline | Visual inspection for insoluble material |
|---|---|---|
| 150 µM variegin (SEQ ID NO: 1) | 72 h | Trace amounts of insoluble material at 48-72 h. |

TABLE 4-continued

Variants of variegin, and their effect on preservation of platelet function and sample solubility (anticoagulation) stability.

| Peptide, concentration | Time after blood draw where aggregation was still measurable above baseline | Visual inspection for insoluble material |
|---|---|---|
| 150 μM Nt29 (SEQ ID NO: 2) | n.d. | Trace insoluble material at 32 h |
| 150 μM Nt26 (SEQ ID NO: 3) | n.d. | Trace insoluble material at 7 h, solidly clotted by 24 h |
| 150 μM Ct29 (SEQ ID NO: 4) | 54-79 h | Trace insoluble material at 48 h |
| 150 μM Ct29 + 1.17 U/ml heparin | 48 h (not measured past 48 h) | None or trace insoluble by 120 h |
| 150 μM Ct22 (SEQ ID NO: 5) | n.d. | Trace to solid clotting in just 1 h |
| 150 μM K10A (SEQ ID NO: 6) | n.d. | Solid clots by 4 h |

As indicated by the data, shortening of the variegin sequence resulted in shorter duration of sample stability, especially as judged by the time of room temperature dwell until a visually detectable amount of insoluble material was formed in the whole blood sample. Nonetheless, shortened variegin sequences may be used to achieve preservation of platelet function in situations where shorter times for overall sample stability might be sufficient, such as in in-hospital or emergency department situations where platelet testing may be performed relatively soon after blood draw.

Two of these variegin analogs (SEQ ID NOs:6 and 16) were used to examine the platelet function preservation abilities of the products when variegin is ultimately cleaved by thrombin. Variegin competes for binding of the active site of thrombin and, as such, is itself subject to cleavage by thrombin (Koh et al., J. Biol. Chem. 282 (40):29101-13 (2007)). Also, mutation of the scissile residue, the lysine in position 10, to an alanine, blocks the ability of thrombin to cleave the peptide designated as SEQ ID NO:6, which resulted in samples solidly clotting within 4 hours after blood draw. Similarly, addition of Ct22, which represents only the 22 carboxy-terminal residues that result after thrombin has cleaved variegin, results in an almost unusable sample that clots solidly within one hour, essentially what would happen if nothing at all was added to the blood and it was allowed to clot on its own after phlebotomy.

These results are inconsistent with the findings reported in Koh, which reports that Ct22, in particular, is an effective thrombin inhibitor for therapeutic purposes, as measured by traditional enzymological experiments. The present results taken in this context, underscore the unpredictability in the art in the sense that the extent of thrombin inhibition for therapeutic purposes is not necessarily predictive of (or does not necessarily correlate with) thrombin inhibition for purposes of stabilizing blood and its components such as platelets under non-physiological conditions such as in a collected blood sample.

The data also show that the combination of Ct29 and 1.17 U/ml heparin extended the hours of sample stability.

EXAMPLE 5

Examination of the Preservation of Platelet Function Provided by Other Direct or Indirect Thrombin Inhibitors A number of direct or indirect thrombin inhibitors were evaluated for their ability to stabilize blood samples, by preserving platelet function, either alone or in combination with other inhibitors. Measurements of platelet aggregation were performed as described in previous examples, using collagen and/or ADP as the platelet agonist, and following manufacturer's suggested protocols.

In addition to variegin, direct thrombin inhibitors examined were argatroban, FM-19, aprotinin, and D-phenylalanyl-L-prolyl-L-arginine chloromethyl ketone (PPACK).

Indirect thrombin inhibitors examined were heparin and sucrose octasulfate (SOS).

All inhibitors were tested for their ability to preserve platelet function in collected blood samples, either alone or in combination with variegin (SEQ ID NO:1).

The results are shown in Table 5 which lists additives alone or in combination that were spiked into freshly drawn whole blood samples. Three performance parameters are reported in this table, namely: 1) the longest time after blood draw at which a reliable platelet aggregation measurement could be made above the baseline of the aggregometer; 2) the earliest time at which visual detection of insoluble material was observed (which includes a qualitative description of the extent of insolubility, either as trace (a low level of detectable material, requiring careful visual observation) or moderate (easily seen upon cursory evaluation) amounts, and then fully clotted samples (solidified as with any undisturbed serum sample, and generally not usable in any way for platelet aggregation measurements); and 3) a qualitative estimate of hemolysis, as determined visually, which is a common and accepted practice in clinical laboratories. For some of the conditions tested, only a subset of these three parameters was recorded.

TABLE 5

| | Additive recipe | Time after blood draw where aggregation was still measurable above baseline | Visual inspection for insoluble material | Visual inspection for hemolysis |
|---|---|---|---|---|
| A | 150 μM variegin | 72 h | Trace at 48-72 h. Solid clots by 96 h | None-mild |
| D | 150 μM variegin + 1.17/ml USP units unfractionated heparin | 72-96 h | Trace at 72-96 h. | None-mild |
| E | 150 μM variegin + 1 mM SOS | | Trace at 72 h | None-mild |
| F | 150 μM variegin + 1 mM SOS + 1.17 U/ml heparin | | None at 72 h | None-mild |
| G | 30 μM Thrombostatin (FM-19) | Not determined | Solidly clotted by 24 h | None-mild |
| H | 150 μM variegin + 30 μM Thrombostatin | 72 h | Trace at 72 h | None-mild |

TABLE 5-continued

| | Additive recipe | Time after blood draw where aggregation was still measurable above baseline | Visual inspection for insoluble material | Visual inspection for hemolysis |
|---|---|---|---|---|
| | (FM-19) | | | |
| I | 2 mM SOS | 72 h | None at 96 h | None-mild |
| J | 150 µM variegin + 2 mM SOS | 72 h | None at 96 h | None-mild |
| | Argatroban, 100 µM + variegin 150 µM | 48 h | Trace at 48 h | Extensive |
| | Argatroban, 100 µM | 24 h | Moderate at 24 h, solid clotts starting at 32 h | Extensive |
| | Argatroban, 50 µM + variegin 150 µM | 48 h | Trace at 48 h | None |
| | Argatroban, 50 µM | 30 h | Moderate or worse by 30 h | Mild-moderate |
| | Argatroban, 75 µM + variegin 150 µM | 72 h | Trace by 72-96 h | Mild by 32 h |
| | Argatroban, 75 µM | 24 h | Moderate at 24 h, solid clots starting at 32 h | Moderate-extensive |
| | Aprotinin 500 KIU/mL + variegin 150 µM | 48 h | Trace to moderate at 24 h, solid clots at 48 h | None-mild |
| | PPACK 75 µM | n.d. | Solid clots at 24 h | |
| | PPACK 75 µM + variegin 150 µM | 48 h | Trace at 32 h, solid clots at 48 h | |

As shown in Table 5, 150 µM variegin and 2 mM SOS, both alone and in combination, proved effective with respect to all three performance metrics. These embodiments of the present invention achieved long timeframes for stability (i.e., at least 72 hours) and largely in the absence of the less desirable attributes of insoluble matter formation and hemolysis.

In stark contrast, several of the direct thrombin inhibitors when used alone, at recommended concentrations or at concentrations reported as therapeutically useful, provided little or no stabilization benefit. In particular, FM-19, CTI and PPACK resulted in extensive insoluble material if not outright solid clotting within 24 h after drawing the blood. Similarly, use of relatively high concentration of argatroban resulted in faster onset of clotting, and less time for stability of the sample for platelet aggregation measurements, as well as extensive amounts of hemolysis. Also, heparin, used alone at 1.17 U/ml, which is approximately one-thirteenth (1/13) of the dosing in a typical heparin plasma sample, performed relatively poorly (data not shown).

These results further underscore the unpredictability with respect to use of known thrombin inhibitors and anticoagulants for stabilizing blood (e.g., preserving platelet function) in vitro, and thus are consistent with Applicants' working hypotheses that stabilization of blood, and particularly blood clotting, at least in the context of an in vitro blood sample, has a different and perhaps more complicated biological/biochemical set of requirements, as compared to evaluation of these inhibitors against simpler systems such as studies of inhibition of purified thrombin without the presence of the rest of the blood components. Furthermore, much of what has been studied about direct thrombin inhibitors concerns potential therapeutic efficacy for treatment of clotting disorders, but, importantly, that such studies and ultimately the underlying biochemical factors associated with making a successful therapeutic dose are not necessarily relevant or prognostic with respect to their capability to stabilize blood components such as platelets in a collected, especially over a period of many hours or days. Stated differently, just because an agent is known for use medicinally as a thrombin inhibitor, both in identity and the appropriate concentrations for efficacy, does not necessarily mean that it will function as an effective blood stabilization agent for purposes of in vitro testing.

On the other hand, the results show that even though these other agents were poorly effective or nearly ineffective when used alone, they provided an additive platelet stabilization effect when used in combination with the inventive embodiments—variegin and SOS. For example, in the case of heparin with variegin, we observed longer times for stability for aggregation measurements and reduced or delayed formation of insoluble material in the whole blood sample. Similar observations were made with FM-19 in combination with variegin. For FM-19 and SOS, the combination with variegin also was seen to slightly increase the overall platelet aggregation signal measured, across the entire timeframe of the experiments. Thus, the observed results show that the activities and ultimately the additive benefits provided by these inhibitors (which in many cases were known to exert their effect by binding the same region in thrombin), when used in vitro to stabilize drawn blood samples, were different than their activity in model enzymological systems designed to evaluate their actual inhibitory potential for therapeutic purposes.

EXAMPLE 6

Comparison Between Inventive Embodiment and Hirudin

Relative stability of platelets was examined in blood that was collected from 5 different human subjects using an inventive blood collection tube containing 150 µM variegin (SEQ ID NO:1)+1.17 USP/mL unfractionated heparin, and as a comparison, blood collection tubes containing hirudin, commercially available from Verum Diagnostica (Catalog #MP0600 for "Hirudin vacuum blood collection tube"). Experiments were carried out as described above in Example 1, using the whole blood impedance aggregometer, and using a low dose of ADP (1.25 µM final concentration) as the agonist.

As shown in Table 6, the platelet function measurements were stronger in the inventive collection tube than in the comparative, non-inventive hirudin samples, both immediately and after 24 hours.

TABLE 6

Platelet aggregation measurements using low dose ADP agonist.

| | | Aggregation, AUC | |
|---|---|---|---|
| | | Inventive tube | Hirudin |
| 0 hr | Subject 1 | 58 | 34 |
| | Subject 2 | 51 | 18 |
| | Subject 3 | 88 | 84 |
| | Subject 4 | 120 | 113 |
| | Subject 5 | 67 | 59 |
| 24 hr | Subject 1 | 32 | 27 |
| | Subject 2 | 26 | 15 |
| | Subject 3 | 33 | 25 |
| | Subject 4 | 32 | 22 |
| | Subject 5 | 44 | 37 |

With fresh blood, tested within one hour of draw, the measurable ADP-induced platelet aggregation averaged 56% higher for blood in the inventive blood collection tube than the blood collected in the tube containing hirudin. Those same samples at 24 hours showed an average of 38% higher activity for the same comparison. The hirudin samples also showed a wider distribution at time zero than the inventive formulation. The 5 hirudin samples showed aggregation of 62+/−38, representing a standard error of approximately 61% (38/62*100). By contrast, aggregation in the inventive tube was 77+/−28, for a standard error of just 36%. These results demonstrate that use of the inventive blood collection devices achieved a more uniform response across a human sample population with improved assay reproducibility. These advantages lead to improved clinical utility for platelet function measurements. For example, by making a smaller range of "normal" for a healthy population, samples with outlying aggregation, which may reflect disease or poor response to anti-platelet drugs, might be easier to detect.

The inventive embodiment, variegin, like hirudin, is a peptide obtained from blood-eating animals. Once again, however, the data demonstrate that such naturally derived direct thrombin inhibitors, as a class, do not have equal or in some cases, near similar efficacy as blood additives, particularly for platelet function analyses, and that their capabilities in this respect are not predictable.

It is also important to consider further ways in which data such as in Table 6 might be utilized. For example, introduction of platelet antagonists would be expected to extensively reduce unantagonized signals, such as reported in Table 6, at least in cases of patients who are properly responsive to the drug/antagonist. Relevant antagonists would include anti-platelet drugs such as aspirin, Plavix and the others already discussed. From previous experiments, addition of 2MeSAMP may result in as much as 50% or more, e.g., 67% (about ⅔) of agonist-induced platelet aggregation, which results in a low signal that can prove difficult to reliably measure above the lower limit of detection of an aggregation instrument. Any measurement in the presence of 2MeSAMP that falls near or below this operational lower limit may not be measurable. In terms of the apparatus used in these experiments, the lower limit of reliable signal is in the range of 8 or 9 AUC. Thus, at least for purposes of the particular instrument used to conduct this experiment, an unantagonized ADP-induced aggregation measurement of at least about 27 AUC may be considered the minimum reliable signal (a 67% drop from 27 AUC would be 9 AUC, which is at the detection limit of this particular instrument). Thus the threshold of 27 AUC is a metric that the data in Table 6 should be judged against.

In one of the five hirudin samples, the area under the curve for the 1 h sample was measured as 18, falling below this functional threshold of 27 and thus would result in a clinically unmeasurable reading in the presence of 2MeSAMP. At 24 h, three of the five hirudin samples fell below 27 AUC, and a fourth was exactly at 27.

In contrast, all five of the samples collected in the inventive blood collection tube maintained platelet aggregation well above the 27 threshold at time 1 h, and four of five at 24 h. This results demonstrates that the present invention stabilizes platelets during collection and subsequent storage that facilitates unambiguous determination of clinically relevant platelet function data, especially in cases where it is important to accurately measure low levels of aggregation, improving the likelihood of measuring usable data over time (such as over hirudin both in fresh samples and samples stored for 24 h).

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for collecting and stabilizing platelet function in a collected blood sample, wherein the device has a first end and a second end and at least one interior wall defining a reservoir portion for receiving the blood sample, wherein the reservoir comprises an anti-coagulant and a platelet stabilization agent comprising variegin having an amino acid sequence designated as SEQ ID NO: 1, or a fragment thereof, wherein the fragment is selected from the group consisting of SEQ ID NOS: 2-5 and analogs of such fragments, the analog fragments selected from the group consisting of SEQ ID NOS: 6-16, either alone or in combination with a polysulfated disaccharide each in an amount effective to stabilize platelets in the blood collected by the device for at least about twenty-four hours, wherein the device is sterile, at least partially evacuated and which further comprises a closure pierceable by a needle.

2. The device of claim 1, which is evacuated.

3. The device of claim 1, which is a tube.

4. The device of claim 3, which further comprises a separator.

5. The device of claim 1, wherein the variegin is present in the device in a concentration of about 1 μm to about 1 mM.

6. The device of claim 1, wherein the polysulfated disaccharide is sucrose octasulfate.

7. The device of claim 1, wherein the platelet stabilization agent comprises the polysulfated disaccharide and which is present in the device in a concentration of about 50 μm to about 50 mM.

8. The device of claim 1 further comprises a direct thrombin inhibitor.

9. The device of claim 8, wherein the direct thrombin inhibitor is selected from the group consisting of argatroban, rOicPaF(p-Me)—NH$_2$, hirudin, bivalirudin, aprotinin, and D-phenylalanyl-L-prolyl-L-arginine (PPACK), and combinations of two or more thereof.

10. The device of claim 1 further comprises an indirect thrombin inhibitor.

11. The device of claim 10, wherein the indirect thrombin inhibitor is selected from the group consisting of heparin and low molecular-weight heparins.

12. The device of claim 1, wherein the platelet stabilization agent is in dried form.

13. The device of claim 1, wherein the anti-coagulant is selected from the group consisting of antistasin, argatroban, E-76, antithrombin III, Factor Xa inhibitors, Factor VII inhibitors, Factor IX inhibitors, Fractor XII inhibitors and Factor II inhibitors, and combinations of two or more thereof.

14. The device of claim 13, wherein the Factor Xa inhibitors are selected from the group consisting of 6-(4-{1-[(dimethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one; and 1-(4-methoxyphenyl)-6-[4-[1-(pyrrolidin-1-ylmethyl)cyclopropyl]phenyl]-3-(trifluoromethyl)-4,5-dihydropyrazolo[3,4-c]pyridin-7-one, and combinations thereof.

15. The device of claim 1, wherein the reservoir further comprises a platelet antagonist.

16. The device of claim 15, where the platelet antagonist is selected from the group consisting of cyclooxygenase inhibitors, P2Y12 inhibitors, and anti-platelet antibodies, and combinations of two or more thereof.

* * * * *